(12) United States Patent
Seed et al.

(10) Patent No.: US 7,518,033 B2
(45) Date of Patent: Apr. 14, 2009

(54) METHODS FOR THE PRODUCTION OF CELLS AND MAMMALS WITH DESIRED GENETIC MODIFICATIONS

(75) Inventors: Brian Seed, Boston, MA (US); Yi Yang, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 28 days.

(21) Appl. No.: 10/521,634

(22) PCT Filed: Aug. 1, 2003

(86) PCT No.: PCT/US03/24322

§ 371 (c)(1),
(2), (4) Date: Oct. 11, 2005

(87) PCT Pub. No.: WO2004/013299

PCT Pub. Date: Feb. 12, 2004

(65) Prior Publication Data

US 2006/0088898 A1 Apr. 27, 2006

Related U.S. Application Data

(60) Provisional application No. 60/400,900, filed on Aug. 2, 2002.

(51) Int. Cl.
*A01K 67/00* (2006.01)
*A01K 67/033* (2006.01)
*A01K 67/027* (2006.01)

(52) U.S. Cl. .......................... 800/21; 800/8; 800/18

(58) Field of Classification Search .................. 800/21, 800/8, 18
See application file for complete search history.

(56) References Cited

U.S. PATENT DOCUMENTS

| | | | |
|---|---|---|---|
| 4,994,384 A | 2/1991 | Prather et al. |
| 5,057,420 A | 10/1991 | Massey |
| 5,453,366 A | 9/1995 | Sims et al. |
| 5,464,764 A | 11/1995 | Capecchi et al. |
| 5,527,674 A | 6/1996 | Guerra et al. |
| 5,595,760 A | 1/1997 | Cherif-Cheikh |
| 5,614,396 A | 3/1997 | Bradley et al. |
| 5,672,659 A | 9/1997 | Shalaby et al. |
| 5,843,972 A | 12/1998 | Dow et al. |
| 5,945,577 A | 8/1999 | Stice et al. |
| 5,998,209 A | 12/1999 | Jokobovits et al. |
| 6,077,710 A | 6/2000 | Susko-Parrish et al. |
| 6,090,554 A | 7/2000 | Woychik et al. |
| 6,090,629 A | 7/2000 | Woychik |
| 6,258,998 B1 | 7/2001 | Damiani et al. |
| 6,355,412 B1 | 3/2002 | Stewart et al. |
| 6,509,156 B1 | 1/2003 | Stewart et al. |
| 6,700,018 B2 | 3/2004 | Richelson et al. |
| 6,747,048 B2 | 6/2004 | Zhang et al. |
| 6,831,102 B2 | 12/2004 | Hangeland |
| 2003/0144341 A1 | 7/2003 | Renshaw et al. |
| 2004/0063694 A1 | 4/2004 | Browder |
| 2004/0097555 A1 | 5/2004 | Ohkawa et al. |
| 2004/0097589 A1 | 5/2004 | Yi-Lin et al. |

OTHER PUBLICATIONS

Wilson (Analytical Biochem., Sep. 15, 2001, vol. 296, No. 2, p. 270-278).*
Angrand (Nucleic Acids Res., 1999, vol. 27, No. 17, e16, i-vi).*
Copeland (Nature Reviews, Genetics, Oct. 2001, vol. 2, p. 769-779).*
Heintz (Nature Reviews, Neurosci., Dec. 2001, vol. 2, p. 861-870).*
Murphy (J. Bacteriology, Apr. 1998, vol. 180, No. 8, p. 2063-2071).*
Muyrers (Trends in Biochemical Sci., May 2001, vol. 26, p. 325-331).*
Testa (Nature Biotech., Apr. 2003, vol. 21, p. 443-447).*
Tsuzuki (Nucleic Acids Res., 1998, vol. 26, No. 4, p. 988-993).*
Yang (Nature Biotech., Sep. 1997, vol. 15, p. 859-865).*
Yang (Nature Biotech., Apr. 2003, vol. 21, p. 447-451).*
Yu (PNAS, May 23, 2000, vol. 97, No. 11, p. 5978-5983).*
Zhang (Nature Genetics, Oct. 1998, vol. 20, p. 123-128).*
Alcalay et al., "Common Themes in the Pathogenesis of Acute Myeloid Leukemia," *Oncogene* 20:5680-5694 (2001).
Angrand et al., "Simplified Generation of Targeting Constructs Using ET Recombination," *Nucleic Acids Res.* 27:e16, i-vi (1999).
Arvand and Denny, "Biology of EWS/ETS Fusions in Ewing's Family Tumors," *Oncogene* 20:5747-5754 (2001).
Aspland et al., "The Role of E2A-PBX1 in Leukemogenesis," *Oncogene* 20:5708-5717 (2001).
Barr "Gene Fusions Involving PAX and FOX Family Members in Alveolar Rhabdomyosarcoma," *Oncogene* 20:5736-5746 (2001).
Benton and Davis, "Screening λgt Recombinant Clones by Hybridization to Single Plaques In Situ," *Science* 196:180-182 (1977).
Bergsagel and Kuehl, "Chromosome Translocations in Multiple Myeloma," *Oncogene* 20:5611-5622 (2001).

(Continued)

*Primary Examiner*—Michael C. Wilson
(74) *Attorney, Agent, or Firm*—Clark & Elbing LLP

(57) ABSTRACT

The present invention features novel methods for generating cell lines and mammals with site-specific genetic modifications of interest. The methods involve homologous recombination between an artificial chromosome having a modification of interest and an endogenous chromosome of a cell. The resulting modified cells can be used in standard methods to generate genetically modified mammals. These mammals can be used in a variety of screening methods to identify compounds useful for the treatment or prevention of disease. Additionally, cells that have been modified to eliminate a mutation associated with a disease can be transplanted into patients for the treatment of a disease.

14 Claims, 28 Drawing Sheets

OTHER PUBLICATIONS

Bollag et al., "Homologous Recombination in Mammalian Cells," *Annu. Rev. Genet.* 23:199-225 (1989).

Bower "Acquired Immunodeficiency Syndrome-Related Systemic Non-Hodgkin's Lymphoma," *Br. J. Haematol.* 112:863-873 (2001).

Boxer and Dang, "Translocations Involving c-Myc and c-Myc Function," *Oncogene* 20:5595-5610 (2001).

Capecchi "Altering the Genome by Homologous Recombination," *Science* 244:1288-1292 (1989).

Capecchi "Choose Your Target," *Nat. Genet.* 26:159-161 (2000).

Chakraborty et al., "Genetic Lesions and Perturbation of Chromatin Architecture: A Road to Cell Transformation," *J. Cell. Biochem.* 82:310-325 (2001).

Chen et al., "Genotype-Based Screen for ENU-Induced Mutations in Mouse Embryonic Stem Cells," *Nat. Genet.* 24:314-317 (2000).

Crans and Sakamoto, "Transcription Factors and Translocations in Lymphoid and Myeloid Leukemia," *Leukemia* 15:313-331 (2001).

Davila et al., "A Role for Secondary V(D)J Recombination in Oncogenic Chromosomal Translocations?," *Adv. Cancer Res.* 81:61-92 (2001).

DeChiara "Gene Targeting in ES Cells," *Methods Mol. Biol.* 158:19-45 (2001).

Deng and Capecchi, "Reexamination of Gene Targeting Frequency as a Function of the Extent of Homology Between the Targeting Vector and the Target Locus," *Mol. Cell. Biol.* 12:3365-3371 (1992).

Dierlamm et al., "Genetic Abnormalitites in Marginal Zone B-Cell Lymphoma," *J. of Hematology.* 88:8-12 (2003).

Drexler et al., "Pathobiology of NPM-ALK and Variant Fusion Genes in Anaplastic Large Cell Lymphoma and Other Lymphomas," *Leukemia* 14:1533-1559 (2000).

Durrant et al., "The Medical Research Council Trials in Adult Acute Lymphocytic Leukemia," *Hematol. Oncol. Clin. North Am.* 14:1327-1352 (2000).

Duyster et al., "Translocations Involving Anaplastic Lymphoma Kinase (ALK)," *Oncogene* 20:5623-5637 (2001).

Dyer and Oscier, "The Configuration of the Immunoglobulin Genes in B Cell Chronic Lymphocytic Leukemia," *Leukemia* 16:973-984 (2002).

El Karoui et al., "Gene Replacement with Linear DNA in Electroporated Wild-Type *Escherichia coli*," *Nucleic Acids Res.* 27:1296-1299 (1999).

Faderi and Albitar, "Insights into the Biologic and Molecular Abnormalities in Adult Acute Lymphocytic Leukemia," *Hematol. Oncol. Clin. North Am.* 14:1267-1288 (2000).

Falini and Mason, "Proteins Encoded by Genes Involved in Chromosomal Alterations in Lymphoma and Leukemia: Clinical Value of their Detection by Immunocytochemistry," *Blood* 99:409-426 (2002).

Falini "Anaplastic Large Cell Lymphoma: Pathological, Molecular and Clinical Features," *Br. J. Haematol.* 114:741-760 (2001).

Garcia-Manero and Kantarjian, "the Hyper-CVAD Regimen in Adult Acute Lymphocytic Leukemia," *Hematol. Oncol. Clin. North Am.* 14:1381-1396 (2000).

Gojo and Karp, "The Impact of Biology on the Treatment of Secondary AML," *Cancer Treat. Res.* 108:231-255 (2001).

Grunstein and Hogness, "Colony Hybridization: A Method for the Isolation of Cloned DNAs that Contain a Specific Gene," *Proc. Natl. Acad. Sci. U.S.A.* 72:3961-3965 (1975).

Hasty et al., "The Length of Homology Required for Gene Targeting in Embryonic Stem Cells," *Mol. Cell. Biol.* 11:5586-5591 (1991).

Holyoake "Recent Advances in the Molecular and Cellular Biology of Chronic Myeloid Leukaemia: Lessons to be Learned from the Laboratory," *Br. J. Haematol.* 113:11-23 (2001).

Hrabè de Angelis et al., "Genome-Wide, Large-Scale Production of Mutant Mice by ENU Mutagenesis," *Nat. Genet.* 25:444-447 (2000).

Kelly et al., "Comprehensive Genotypic Analysis of Leukemia: Clinical and Therapeutic Implications," *Curr. Opin. Oncol.* 14:10-18 (2002).

Kuehl and Bergsagel, "Multiple Myeloma: Evolving Genetic Events and Host Interactions," *Nat. Rev. Cancer* 2:175-187 (2002).

Küppers and Dalla-Favera, "Mechanisms of Chromosomal Translocations in B Cell Lymphomas," *Oncogene* 20:5580-5594 (2001).

Kyba et al., "HoxB4 Confers Definitive Lymphoid-Myeloid Engraftment Potential on Embryonic Stem Cell and Yolk Sac Hematopoietic Progenitors," *Cell* 109:29-37 (2002).

Lamorte and Park, "The Receptor Tyrosine Kinases: Role in Cancer Progression," *Surg. Oncol. Clin. N. Am.* 10:271-288 (2001).

Larson "Recent Clinical Trials in Acute Lymphocytic Leukemia by the Cancer and Leukemia Group B," *Hematol. Oncol. Clin. North Am.* 14:1367-1379 (2000).

Lee "Chronic Myelogenous Leukaemia," *Br. J. Haematol.* 111:993-1009 (2000).

Licht "AML1 and the AML1-ETO Fusion Protein in the Pathogenesis of t(8;21) AML," *Oncogene* 20:5660-5679 (2001).

Loots et al., "Identification of a Coordinate Regulator of Interleukins 4, 13, and 5 by Cross-Species Sequence Comparisons," *Science* 288:136-140 (2000).

Maru "Molecular Biology of Chronic Myeloid Leukemia," *Int. J. Hermatol.* 73:308-322 (2000).

Mavrothalassitis and Ghysdael, "Proteins of the ETS Family with Transcriptional Repressor Activity," *Oncogene* 19:6524-6532 (2000).

Morris et al., "Alk$^+$ CD30$^+$ Lymphomas: A Distinct Molecular Genetic Subtype of Non-Hodgkin's Lymphoma," *Br. J. Haematol.* 113:275-295 (2001).

Müllauer et al., "Mutations in Apoptosis Genes: A Pathogenetic Factor for Human Disease," *Mutat. Res.* 488:211-231 (2001).

Munroe et al., "Mouse Mutants from Chemically Mutagenized Embryonic Stem Cells," *Nat. Genet.* 24:318-321 (2000).

Murphy "Use of Bacteriophage Lambda Recombination Functions to Promote Gene Replacement in *Escherichia coli*," *J. Bacteriol.* 180:2063-2071 (1998).

Muyrers et al., "Rapid Modification of Bacterial Artificial Chromosomes by ET-Recombination," *Nucleic Acids Res.* 27:1555-1557 (1999).

Nefedov et al., "Insertion of Disease-Causing Mutations in BACs by Homologous Recombination in *Escherichia coli*," *Nucleic Acids Res.* 28:e79, i-iv (2000).

Nolan et al., "A Systematic, Genome-Wide, Phenotype-Driven Mutagenesis Programme for Gene Function Studies in the Mouse," *Nat. Genet.* 25:440-443 (2000).

Padua et al., "Molecular, Cytogenetic and Genetic Abnormalities in MDS and Secondary AML," *Cancer Treat. Res.* 108:111-157 (2001).

Papakostas et al., "Cholesterol in Mood and Anxiety Disorders: Review of the Literature and New Hypotheses," *Eur. Neuropsychopharmacol.* 14:135-142 (2004).

Pavan et al., "Modification and Transfer into an Embryonal Carcinoma Cell Line of a 360-Kilobase Human-Derived Yeast Artificial Chromosome," *Mol. Cell. Biol.* 10:4163-4169 (1990).

Pennacchio et al., "An Apolipoprotein Influencing Triglycerides in Humans and Mice Revealed by Comparative Sequencing," *Science* 294:169-173 (2001).

Poteete and Fenton, "λ red-Dependent Growth and Recombination of Phage P22," *Virology* 134:161-167 (1984).

Pui and Relling, "Topoisomerase II Inhibitor-Related Acute Myeloid Leukaemia," *Br. J. Haematol.* 109:13-23 (2000).

Ramirez-Solis et al., "Chromosome Engineering in Mice," *Nature* 378:720-724 (1995).

Reid et al., "Cotransformation and Gene Targeting in Mouse Embryonic Stem Cells," *Mol. Cell. Biol.* 11:2769-2777 (1991).

Rideout et al., "Correction of a Genetic Defect by Nuclear Transplantation and Combined Cell and Gene Therapy," *Cell* 109:17-27 (2002).

Ruediger et al., "Disruption of Protein Phosphatase 2A Subunit Interaction in Human Cancers with Mutations in the Aα Subunit Gene," *Oncogene* 20:10-15 (2001).

Sattler and Griffin, "Mechanisms of Transformation by the BCR/ABL Oncogene," *Int. J. Hematol.* 73:278-291 (2001).

Seidel and Look, "E2A-HLF Usurps Control of Evolutionarily Conserved Survival Pathways," *Oncogene* 20:5718-5725 (2001).

Smith et al., "Cre-loxP Chromosome Engineering of a Targeted Deletion in the Mouse Corresponding to the 3p21.3 Region of Homozygous Loss in Human Tumours," *Oncogene* 21:4521-4529 (2002).

Stevenson et al., "The Occurrence and Significance of V Gene Mutations in B Cell-Derived Human Malignancy," *Adv. Cancer Res.* 83:81-116 (2001).

Stice and Keefer, "Multiple Generational Bovine Embryo Cloning," *Biol. Reprod.* 48:715-719 (1993).

Stürzl et al., "Human Herpesvirus-8 and Kaposi's Sarcoma: Relationship with the Multistep Concept of Tumorigenesis," *Adv. Cancer Res.* 81:125-159 (2001).

Swerdlow and Williams, "From Centrocytic to Mantle Cell Lymphoma: A Clinicopathologic and Molecular Review of 3 Decades," *Hum. Pathol.* 33:7-20 (2002).

Testa et al., "Engineering the Mouse Genome with Bacterial Artificial Chromosomes to Create Multipurpose Alleles," *Nat. Biotechnol.* 21:443-447 (2003).

Thiebaut et al., "Adult Acute Lymphocytic Leukemia Study Testing Chemotherapy and Autologous and Allogeneic Transplantation. A Follow-up Report of the French Protocol LALA 87," *Hematol. Oncol. Clin. North Am.* 14:1353-1366 (2000).

Thyagarajan et al., "Characterization of Homologous DNA Recombination Activity in Normal and Immortal Mammalian Cells," *Nucleic Acids Res.* 24:4084-4091 (1996).

Tsuzuki and Rancourt, "Embryonic Stem Cell Gene Targeting Using Bacteriophage Lambda Vectors Generated by Phage-Plasmid Recombination," *Nucleic Acids Res.* 26:988-993 (1998).

Valenzuela et al., "High-Throughput Engineering of the Mouse Genome Coupled with High-Resolution Expression Analysis," *Nat. Biotechnol.* 21:652-659 (2003).

Wakayama et al., "Mice Cloned from Embryonic Stem Cells," *Proc. Natl. Acad. Sci. U.S.A.* 96:14984-14989 (1999).

Wakayama et al., "Nuclear Transfer into Mouse Zygotes," *Nat. Genet.* 24:108-109 (2000).

Wiles et al., "Establishment of a Gene-Trap Sequence Tag Library to Generate Mutant Mice from Embryonic Stem Cells," *Nat. Genet.* 24:13-14 (2000).

Wilson et al., "Yeast Artificial Chromosome Targeting Technology: An Approach for the Deletion of Genes in the C57BL/6 Mouse," *Anal. Biochem.* 296:270-278 (2001).

Yang et al., "Homologous Recombination Based Modification in *Escherichia coli* and Germline Transmission in Transgenic Mice of a Bacterial Artificial Chromosome," *Nat. Biotechnol.* 15:859-865 (1997).

Yang et al., "Targeted Disruption of the Murine Fanconi Anemia Gene, *Fancg/Xrcc9*," *Blood* 98:3435-3440 (2001).

Yang and Seed, "Site-Specific Gene Targeting in Mouse Embryonic Stem Cells with Intact Bacterial Artificial Chromosomes," *Nat. Biotechnol.* 21:447-451 (2003).

Yokoi et al., "*Cblb* is a Major Susceptibility Gene for Rat Type 1 Diabetes Mellitus," *Nat. Genet.* 31:391-394 (2002).

Yu et al., "An Efficient Recombination System for Chromosome Engineering in *Escherichia coli*," *Proc. Natl. Acad. Sci. U.S.A.* 97:5978-5983 (2000).

Zambrowicz et al., "Disruption and Sequence Identification of 2,000 Genes in Mouse Embryonic Stem Cells," *Nature* 392:608-611 (1998).

Zhang et al., "A New Logic for DNA Engineering Using Recombination in *Escherichia coli*," *Nat. Genet.* 20:123-128 (1998).

Zhang et al., "Towards Genetic Genome Projects: Genomic Library Screening and Gene-Targeting Vector Construction in a Single Step," *Nat. Genet.* 30:31-39 (2002).

Zijlstra et al., "Germ-Line Transmission of a Disrupted $\beta_2$-Microglobulin Gene Produced by Homologous Recombination in Embryonic Stem Cells," *Nature* 342:435-438 (1989).

International Search Report from PCT/US03/24322, mailed Jul. 2, 2004.

\* cited by examiner

| Gene/Clone | 5'arm (nt) | 3'arm (nt) | Deletion (nt) | Efficiency* |
|---|---|---|---|---|
| fancg/xrcc9 | 480 | 260 | 4900 | 100% |
| IκβrasI.#1 | 185 | 138 | unknown | 30% |
| IκβrasI.#2 | 185 | 138 | unknown | 25% |
| tab2.#1 | 213 | 340 | 869 | 30% |
| tab2.#2 | 213 | 340 | 869 | 50% |
| pag.#1 | 105 | 373 | no | 100% |
| pag.#2 | 105 | 373 | no | 58% |
| pag.#3 | 105 | 373 | no | 100% |
| dok3/dok-L#1 | 188 | 93 | no | 42% |
| dok3/dok-L#2 | 188 | 93 | no | 30% |
| bruce | 50 | 50 | no | 100% |

*The efficiency was calculated based on nested PCR screening of 24 ampicillin and chloramphenicol double resistant colonies at the 3' integration site.

Fig. 10

| | PCR screening/96 colonies | | | | | FISH screening | | | Effective targeting efficiency[c] |
|---|---|---|---|---|---|---|---|---|---|
| Gene | no signal[a] | 5' BAC | 3' BAC | 5' & 3' BAC | no BAC signal[b] | colonies screened | 2 spots | 3 spots | |
| FANCG/XRCC9 | 36 | 4 | 6 | 28 | 22 (37%) | 4 | 3 (75%) | 1 | 28% |
| IκβRAS1 | 1 | 16 | 12 | 15 | 52 (55%) | 27 | 6 (22%) | 21 | 12% |
| CBP/PAG | 6 | 10 | 5 | 32 | 43 (48%) | 16 | 7 (44%) | 9 | 21% |
| DOK3/DOK-L | 6 | 12 | 9 | 55 | 14 (16%) | 11 | 5 (45%) | 6 | 7% |
| TAB2 | 16 | 8 | 16 | 27 | 29 (36%) | 10 | 2 (20%) | 8 | 7% | a. A high PCR failure rate (internal control negative) was seen with FANCG/XRCC9 prior to the introduction of improved protocols.
b. Percentage calculation denominator excludes PCR failures.
c. The percentage with no vector signal multiplied by the percentage with two FISH spots.

Fig. 14

METHODS FOR THE PRODUCTION OF CELLS AND MAMMALS WITH DESIRED GENETIC MODIFICATIONS

CROSS REFERENCE TO RELATED APPLICATIONS

This application is the U.S. National Stage of International Application No. PCT/US2003/024322, filed Aug. 1, 2003, which claims the benefit of U.S. Provisional Application No. 60/400,900, filed Aug. 2, 2002.

BACKGROUND

In general, the invention features novel methods for rapidly generating cell lines and mammals with site-specific genetic modifications of interest.

As the human genome sequencing effort approaches completion, much of the research focus has shifted from physical mapping of the genome to functional annotation of its contents. The challenge lies in evolving comprehensive approaches to efficiently define gene functions in vivo. The murine system is ideal for functional genomics because of the underlying biological similarity between human and mouse, the rapid advances in mouse genome sequencing, and the ability to genetically manipulate mouse embryonic stem (ES) cells.

Although gene disruption in mice has been widely used for functional analyses of genes in vivo, traditional procedures for generating site-specific gene knockout mice are generally time-consuming and labor-intensive. For these traditional methods, the targeting construct usually contains 6-10 kb of genomic sequence from the gene of interest with, e.g., a neomycin-resistant ($neo^r$) gene inserted into the coding region and a herpes-virus thymidine kinase (tk) gene placed at one end (FIG. 1A). The targeting construct is electroporated into ES cells and replaces the endogenous locus by homologous recombination. After verification by genomic DNA Blotting or by polymerase chain reaction (PCR) using primers that hybridize to the flanking region and the disrupted gene, ES cells bearing the mutant locus are injected into a mouse blastocyst to generate chimera mice. By either method, the flanking sequences of the replica cannot be too long. Finally, heterozygous and eventually homozygous mutant mice are obtained from the breeding of chimeric animals.

To make the targeting construct often requires fine restriction enzyme mapping of the gene and multi-step cloning, which is a long and tedious process. In order to prevent expression of a partial gene, which can result from alternative splicing, the insertion site should be as close to the translation initiation ATG as possible. This is often hindered by the lack of a convenient cloning site around the desired region. Furthermore, the length of homologous fragments that can be included in the targeting construct is often limited, resulting in low homologous recombination frequency. Data from haplotype mapping of human populations and studies of meiotic and mitotic recombination frequency in lower eukaryotes support the idea that favored sites for initiation of DNA exchange can be separated by up to several tens of kilobases from one another in euchromatin. If these findings are relevant to mitotic recombination in ES cells, it may be necessary to use very long flanking sequences to obtain high frequency homologous recombination. Creating such long flanking arms by conventional cloning is cumbersome and frequently impractical.

Thus, improved methods are needed to more efficiently generate genetically modified cell lines and non-human mammals.

SUMMARY OF THE INVENTION

The purpose of the present invention is to provide improved methods for genetically altering cells. In particular, these methods involve generating a modified artificial chromosome by homologous recombination between an artificial chromosome containing a nucleic acid of interest (e.g., a bacterial or yeast artificial chromosome containing a genomic insert from the same genus or species as the cell to be subsequently modified) and a nucleic acid (e.g., a linear DNA molecule) containing a region or the entire nucleic acid of interest with a desired mutation. In some embodiments, the artificial chromosome is a bacterial artificial chromosome (BAC) or a P1-based artificial chromosome (PAC), and the homologous recombination occurs in bacteria, or the artificial chromosome is a yeast artificial chromosome (YAC), and the homologous recombination occurs in yeast. The resulting modified artificial chromosome with the desired mutation is introduced into one or more cells (e.g., mammalian cells such as mouse, ungulate, or human cells), and the genetically modified cells in which homologous recombination occurs between the artificial chromosome and corresponding region of an endogenous chromosome in the cell are selected.

In some embodiments, the cell is modified to express a reporter gene under the control of an endogenous promoter of interest. In other embodiments, the cell is modified such that an exogenous nucleic acid encoding a detectable protein is operably linked to an endogenous nucleic acid encoding a protein of interest, thereby generating a genetically modified cell that expresses a fusion protein having the detectable protein and the protein of interest or a fragment thereof. These modified cells can be used in a variety of screening assays to identify candidate compounds that modulate the activity of the promoter of interest or the expression of the protein of interest. Additionally, these cells can be used in any standard method for the generation of mammals with one or more desired genetic modifications. These mammals are also useful in screening assays to identify compounds for the treatment or prevention of disease.

Accordingly, in a first aspect the invention provides a method of producing a genetically modified cell. This method involves inserting into one or more cells an artificial chromosome (e.g., a linear BAC, PAC, or YAC) having a cassette which includes a first region of homology having substantial sequence identity to a first region of an endogenous chromosome of the cell(s), a selectable marker, and a second region of homology having substantial sequence identity to a second region of the endogenous chromosome. Homologous recombination occurs between the artificial chromosome and the endogenous chromosome (e.g., homologous recombination between the first region of homology and the first region of the endogenous chromosome and homologous recombination between the second region of homology and the second region of the endogenous chromosome), and the cassette is integrated into the endogenous chromosome of one or more cells. One or more cells are selected in which the homologous recombination occurs, thereby selecting one or more genetically modified cells.

In preferred embodiments, the artificial chromosome having the cassette is produced by a culturing a cell (e.g. a bacterial or yeast cell) that has (i) a linear DNA molecule having the cassette and (ii) an artificial chromosome having nucleic acid that is substantial identical to the first and second regions of homology (e.g., a BAC, PAC, or YAC having a genomic insert from the same genus or species as the cells to be subsequently modified) under conditions that result in homologous recombination between the linear DNA molecule and the artificial chromosome. In particular embodiments for generating the artificial chromosome with the cassette, the linear DNA molecule is introduced into the cell by transformation. In other embodiments, the linear DNA molecule is introduced into the cell by insertion of a circular vector having the sequence of the linear DNA molecule into the cell and cleavage of the vector to generate the linear DNA molecule inside the cell. It is also contemplated that the homologous recombination between the artificial chromosome and the linear DNA molecule can occur in an in vitro sample that has a recombinase that catalyzes homologous recombination. In preferred embodiments, the first and second regions of homology in the linear DNA molecule are less than 2,000, 1,000, 500, 250, 200, 100, 75, 50, or 25 nucleotides in length. In other embodiments, the first and second regions of homology are between 2,000 and 10,000 nucleotides in length, such as between 2,000 and 5,000 nucleotides or between 5,001 and 10,000 nucleotides in length, inclusive. Preferably, the percent sequence identity between the first region of homology in the linear DNA molecule and the corresponding region in the artificial chromosome and the percent sequence identity between the second region of homology in the linear DNA molecule and the corresponding region in the artificial chromosome is at least 90, 92, 94, 96, 98, or 100%. In some embodiments the linear DNA molecule has another region 5' to the first region of homology and/or another region 3' to the second region of homology.

In other embodiments, the first and second regions of the endogenous chromosome are contiguous. In particular embodiments, the first and second regions of the endogenous chromosome are part of the same exon or the same promoter. In other embodiments, the first and second regions of the endogenous chromosome are not contiguous (e.g., the first and second regions of the endogenous chromosome are part of different exons).

In some embodiments, the selectable marker is inserted into an endogenous promoter or coding sequence and reduces the expression or activity of the protein expressed by the nucleic acid; In other embodiments, the cassette (e.g., the first or second region of homology) has a mutation of interest that is incorporated into the endogenous chromosome. Preferably, the integration of the cassette into the genome of the cell reduces the activity of an RNA (e.g., tRNA) or protein encoded by a nucleic acid of interest (e.g., a nucleic acid that includes a region located between or located within the first and second region of the endogenous chromosome that is mutated by integration of the cassette). In preferred embodiments, the amount of functional protein encoded by the nucleic acid of interest decreases by at least 5, 10, 25, 50, 75, 90, 95, or 100%.

In various embodiments, the cassette includes a promoter and/or a polyadenylation signal sequence operably linked to the positive selection maker. In other embodiments, the cassette does not contain a promoter and/or a polyadenylation signal sequence, and the cassette integrates into the genome of the cell such that the positive selection maker is operably linked to an endogenous promoter and/or polyadenylation signal sequence for expression of the selection marker in the cell. In some embodiments, the cassette has two positive selection markers; one selection marker for selection of bacteria or yeast cells with the artificial chromosome having the cassette, and another selection marker for subsequent selection of cells in which a region of the cassette from the artificial chromosome has inserted into the genome. In other embodiments, the cassette has one positive selection marker (e.g., a neomycin resistance gene) operably linked to two different promoters, one promoter for expression of the selection marker in bacteria (e.g., pE7) and another promoter for expression of the selection marker in mouse cells such as embryonic stem cells (e.g., PGK).

In other preferred embodiments, the cassette includes a reporter gene, and the cassette is integrated into the genome of the cell such that the reporter gene is operably linked to an endogenous promoter of interest, thereby generating a genetically modified cell that expresses the reporter gene under the control of the promoter of interest. Exemplary reporter genes include nucleic acids encoding chloramphenicol acetyltransferase, firefly luciferase, renilla luciferase, β-galactosidase, secreted alkaline phosphatase, human growth hormone, β-glucuronidase, green fluorescent protein, or red fluorescent protein. In some embodiments, the method further includes administering one or more compounds to the genetically modified cells and selecting a compound that alters the expression of the reporter gene. This selected compound is useful for modulating the activity of the promoter of interest and thus modulating the expression of endogenous nucleic acids operably linked to the promoter.

In still other preferred embodiments, the cassette includes a nucleic acid encoding a detectable protein (e.g., a fluorescent protein or a protein that catalyzes a reaction in which the reactant or product is detectable), and the cassette is integrated into the genome of the cell such that the nucleic acid is operably linked to an endogenous nucleic acid encoding a protein of interest, thereby generating a genetically modified cell that expresses a fusion protein having the detectable protein and the protein of interest or a fragment thereof. In some embodiments, the nucleic acid encoding the detectable protein replaces a portion of the nucleic acid encoding a protein of interest, thereby generating a fusion nucleic acid that encodes a fusion protein that includes the detectable protein and a fragment of the protein of interest. In other embodiments, the nucleic acid encoding the detectable protein is inserted upstream or downstream of the nucleic acid encoding a protein of interest, thereby generating a fusion nucleic acid that encodes a fusion protein that includes the detectable protein and the entire protein of interest. In some embodiments, the method further includes administering one or more compounds to the genetically modified cells and selecting a compound that alters the expression of the fusion protein. This selected compound is useful for modulating the expression of the protein of interest.

In desirable embodiments, the steps of the method are repeated, thereby generating a genetically modified cell with two or more mutations. The mutations may be in different alleles of the same gene or in different genes. In some embodiments, each cassette has a recombinase signal sequence, thereby generating a genetically modified cell with two recombinase signal sequences. Recombination may occur between the recombinase signal sequences in the cell.

In some embodiments, the recombinase signal sequences are in the same endogenous chromosome of the cell, and recombination between the recombinase signal sequences results in elimination of the DNA between the recombinase signal sequences. In other embodiments, the recombinase signal sequences are in different endogenous chromosomes of the cell, and recombination between the recombinase signal sequences results in chromosomal translocation between the recombinase signal sequences.

In other preferred embodiments of various aspects of the invention, the cell is an adult, fetal, or embryonic cell.

Examples of preferred cells include undifferentiated cells such as embryonic cells (e.g., embryonic stem cells or embryonic germ cells) and differentiated or somatic cells such as epithelial cells, neural cells, epidermal cells, keratinocytes, hematopoietic cells, melanocytes, chondrocytes, B-lymphocytes, T-lymphocytes, erythrocytes, macrophages, monocytes, fibroblasts, and muscle cells. In another preferred embodiment, the cell is from the female reproductive system, such as a mammary gland, ovarian cumulus, granulosa, or oviductal cell. Other preferred cells include germ and placental cells. Preferred cells also include those from any organ, such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus.

The genetically modified cells produced by any of the methods of the invention can be used as donor cells for the production of non-human mammals with one or more desired genetic modifications. In particular, these cells can be used in any standard method for the generation of chimeric or cloned mammals. In some embodiments, a cell is inserted into an embryo (e.g., a blastocyst) or fetus for the generation of a chimeric mammal that contains some cells with the genetic mutation(s) and some cells without the mutation(s). In other embodiments, a cell or a nucleus from the cell is inserted into an oocyte for the generation of a cloned mammal in which most or all of the cells have the genetic mutation(s).

Accordingly, in one such aspect, the invention provides a method of producing a genetically modified non-human mammal (e.g., a mouse) that involves inserting a cell produced by a method of the invention into a non-human embryo under conditions that allow the embryo to develop into a fetus.

In a related aspect, the invention provides another method of producing a genetically modified non-human mammal (e.g., an ungulate). This method involves inserting a cell produced by a method of the invention or a nucleus from the cell into an oocyte. The oocyte or an embryo formed from the oocyte is transferred into the uterus of a host mammal under conditions that allow the oocyte or the embryo to develop into a fetus.

In preferred embodiments of any of the above aspects for generating mammals, the fetus develops into a live offspring. In some embodiments, one or more cells are isolated for the fetus or live offspring, and one or more additional mutations are introduced into the cells. If desired, these cells can be used to generate mammals with these additional modifications. The methods may also involve mating two of the offspring to generate a mammal with a homozygous mutation or a mammal with a mutation in two or more genes.

In some embodiments, the donor cell has two recombinase signal sequences and recombination occurs between the recombinase signal sequences in cells of a predetermined cell type of the fetus or a live offspring formed from the fetus. For example, the donor cell may be genetically modified to encode a recombinase under the control of a promoter specific for the predetermined cell type such that the recombinase is only expressed and recombination only occurs in that cell type of the fetus or offspring.

The mammals produced by the above methods can be used in various screening assays to identify a candidate compound that modulates the expression of a nucleic acid or protein of interest or that is useful for the treatment or prevention of a disease. For example, a candidate compound can be administered to a mammal genetically modified to express a reporter gene under the control of a promoter of interest or to express a fusion protein that includes a detectable protein and a protein of interest. The expression levels of the reporter gene or fusion protein can be measured to determine if the candidate compound modulates their expression in vivo. Such compounds may be useful for the treatment of a disease associated with a nucleic acid operably linked to the promoter of interest or associated with the protein of interest. Additionally, genetically modified mammals having a mutation associated with a disease can be used as animal models for the study of the disease. Compounds can be administered to these animal models to determine whether they ameliorate or prevent a symptom or other physiological effect associated with the disease.

Accordingly, the invention provides a screening method for determining whether a candidate compound modulates the expression of a nucleic acid of interest. This method involves administering a candidate compound to a mammal (e.g., a mammal that has a genetic modification in a nucleic acid of interest or in a promoter operably linked to a nucleic acid of interest) produced by a method of the invention, and measuring the expression of a nucleic acid. The candidate compound is determined to modulate expression of the nucleic acid if the candidate compound causes a change in expression of the nucleic acid. In some embodiments, measuring the expression of the nucleic acid involves measuring the expression of an mRNA corresponding to the nucleic acid or the expression of a protein encoded by the nucleic acid. Preferably, the mammal is genetically modified to express a reporter gene operably linked to a promoter of interest (e.g., a promoter that modulates the expression of a nucleic acid associated with a disease). In other embodiments, the mammal is genetically modified to express a fusion protein that includes a detectable protein and a protein of interest or a fragment thereof. In desirable embodiments, the protein of interest is associated with a disease. Exemplary candidate compounds include, for example, proteins, synthesized organic molecules, naturally occurring organic molecules, nucleic acid molecules, and components thereof. In some embodiments, the candidate compound is a member of a library of at least 5, 10, 25, 50, 100, 500, or more compounds that are simultaneously administered to the mammal.

In another aspect, the invention features a screening method for determining whether a candidate compound is useful for the treatment, stabilization, or prevention of a disease, disorder, or condition. This method involves administering a candidate compound to a mammal produced by a method of the invention, and measuring one or more symptoms associated with the disease, disorder, or condition. The candidate compound is determined to be useful for the treatment, stabilization, or prevention of the disease, disorder, or condition if the candidate compound reduces, stabilizes, or prevents the symptom. In desirable embodiments, the genetically modified cell used to generate the mammal has a mutation associated with a disease, and the mammal has one or more phenotypes or symptoms associated with the disease. In some embodiments, the mammal has a mutation, chromosomal deletion, or translocation associated with cancer. Exemplary candidate compounds include, for example, proteins, synthesized organic molecules, naturally occurring organic molecules, nucleic acid molecules, and components thereof. In some embodiments, the candidate compound is a member of a library of at least 5, 10, 25, 50, 100, 500, or more compounds that are simultaneously administered to the mammal.

The invention also provides a method for determining whether a nucleic acid of interest is associated with a disease, disorder, or condition. This method involves measuring one or more symptoms associated with the disease, disorder, or condition in a mammal that has a mutation in a nucleic acid of interest and that is produced by a method of the invention. The nucleic acid is determined to be associated with the disease, disorder, or condition if the symptom differs between the mammal and a control mammal without the mutation. In some embodiments, a mutation is introduced into an endogenous promoter to increase the expression of a nucleic acid of interest. Exemplary nucleic acids include nucleic acids that are thought to promote cancer such as possible oncogenes; genes that enhance cell proliferation, invasion, or metastasis; genes that inhibit apoptosis; and pro-angiogenesis genes.

The genetically modified cells produced using the methods of the invention can also be administered to a mammal for the treatment, stabilization, or prevention of a disease associated with a deficiency of functional cells of a particular cell-type or associated with a mutation that is not present in the genetically modified cells. For example, the cells can be modified to replace a nucleic acid sequence that is associated with a disease with a nucleic acid sequence that is not associated with a disease.

Accordingly, in one aspect, the invention provides a method of treating, stabilizing, or preventing a disease, disorder, or condition in a mammal (e.g., a human). This method involves administering one or more cells (e.g., purified or unpurified mammalian or human cells) produced by a method of the invention to a mammal in an amount sufficient to treat, stabilize, or prevent the disease, disorder, or condition. In some embodiments, the mammal has a mutation associated with a disease that is not present in the administered cells (e.g., cells that have been genetically modified to eliminate a mutation associated with a disease). Preferably, a disease-causing mutation in a regulatory region, promoter, untranslated region, or coding region of a gene in the cells is modified to replace the mutant sequence with a sequence that is not associated with the disease. Examples of mutations that may be rescued using these methods include dominant or recessive mutations (e.g., mutations in the cystic fibrosis gene or a gene encoding a human clotting factors such as any of factors I to XIII) (Voet and Voet, Biochemistry, John Wiley & Sons, New York, 1990). In other embodiments, the mammal has a deficiency in the number or activity of cells of a certain cell type.

In some embodiments of the therapeutic methods of the invention, the transplanted cells are genetically modified to introduce a mutation in a promoter or regulatory region that increases the expression of an operably linked nucleic acid that encodes a protein that prevents or ameliorates cancer. Cancer related genes that inhibit cancer include, but are not limited to, tumor suppressor genes; genes that inhibit cell proliferation, invasion, or metastasis; genes that promote apoptosis; and anti-angiogenesis genes. Exemplary cancers include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods and cells of the present invention.

With respect to the therapeutic methods of the invention, it is not intended that the administration of genetically modified cells to a mammal be limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. Preferably, the genetically modified cells are administered to the mammal from which the cells are obtained. Alternatively, the cells may be obtained from a different donor mammal of the same or a different genus or species as the recipient mammal. Examples of preferred donor mammals include humans, cows, sheep, big-horn sheep, goats, buffalos, antelopes, oxen, horses, donkeys, mule, deer, elk, caribou, water buffalo, camels, llama, alpaca, rabbits, pigs, mice, rats, guinea pigs, hamsters, dogs, cats, and primates such as monkeys. The cells may be administered to the mammal in a single dose or multiple doses. When multiple doses are administered, the doses may be separated from one another by, for example, one week, one month, one year, or ten years. One or more immunosuppressive agents, such as cyclosporin, may be administered to inhibit rejection of the transplanted cells. It is to be understood that, for any particular subject, specific dosage regimes should be adjusted over time according to the individual need and the professional judgment of the person administering or supervising the administration of the compositions. If desired, conventional treatments may be used in combination with the genetically modified cells of the present invention.

In preferred embodiments of any of the various aspects of the invention, the genetically modified cell has a mutation that alters the expression level or activity of one or more mRNA or protein molecules by at least 2, 5, 10, or 20-fold, as measured using standard assays (see, for example, Ausubel et al., Current Protocols in Molecular Biology, John Wiley & Sons, New York, 2000).

The cells and oocytes used in these methods may be from the same species, or they may be from different species or genuses. In preferred embodiments, the oocyte is an enucleated or nucleated non-human oocyte. In addition, the genomic DNA of the cloned embryo, fetus, or mammal is preferably substantially identical to that of the donor cell. In other embodiments, the donor cell is inserted into an embryo for the production of a chimeric embryo, fetus, or mammal containing a mixture of (i) cells with DNA substantially identical to that of the genetically modified donor cell and (ii) cells with DNA substantially identical to that of the naturally-occurring cells in the embryo. Preferred non-human mammals and preferred sources of cells include rodents, such as mice and rats. Examples of other preferred mammals and preferred sources of cells include cows, sheep, big-horn sheep, goats, buffalos, antelopes, oxen, horses, donkeys, mule, deer, elk, caribou, water buffalo, camels, llama, alpaca, rabbits, pigs, guinea pigs, hamsters, and primates such as monkeys. In some embodiments, the mammal is a murine or an ungulate such as a bovine, ovine, porcine, or caprine.

As used herein, by "artificial chromosome" is meant a chromosome or fragment thereof which has an artificial (i.e., non-naturally occurring or engineered) modification such as the addition of a selectable marker, the addition of a cloning site, the deletion of one or more nucleotides, the substitution of one or more nucleotides, or the like. By "bacterial artificial chromosome (BAC)" is meant an artificial chromosome generated from a low copy plasmid capable of faithfully replicating large chromosomal segments. Similarly, by "yeast cartificial chromosome (YAC)" is meant an artificial chromosome generated from one or more yeast chromosomes. By "P1-based artificial chromosome (PAC)" is meant an artificial chromosome generated from the latent replicon of phage P1. If desired, two or more artificial chromosomes can be introduced into a cell (e.g., a bacteria or yeast) simultaneously or sequentially using standard methods (see, for example, Ausubel et al., Current Protocols in Molecular Biology, John Wiley & Sons, New York, 2000).

By "donor cell" is meant a cell from which genetic material (e.g., the nucleus or the entire cell) is inserted into an oocyte, embryo, or fetus for the generation of a mammal with a genetic modification.

By "purified" is meant separated from other components that naturally accompany it. Typically, a factor or cell is substantially pure when it is at least 50%, by weight, free from proteins, antibodies, naturally-occurring organic molecules, and cells with which it is naturally associated. Preferably, the factor or cell is at least 75%, more preferably, at least 90%, and most preferably, at least 99%, by weight, pure. A substantially pure factor may be obtained by chemical synthesis, separation of the factor from natural sources, or production of the factor in a recombinant host cell that does not naturally produce the factor. Proteins, vesicles, organelles, and cells may be purified by one skilled in the art using standard techniques such as those described by Ausubel et al. (Current Protocols in Molecular Biology, John Wiley & Sons, New York, 2000). The factor or cell is preferably at least 2, 5, or 10 times as pure as the starting material, as measured using polyacrylamide gel electrophoresis, column chromatography, optical density, HPLC analysis, or western analysis (Ausubel et al., supra). Preferred methods of purification include immunoprecipitation, column chromatography such as immunoaffinity chromatography, magnetic bead immunoaffinity purification, panning with a plate-bound antibody, and cell sorting.

By "viable offspring" is meant a mammal that survives ex utero. Preferably, the mammal is alive for at least one second, one minute, one hour, one day, one week, one month, six months, or one year from the time it exits the maternal host. The mammal does not require the circulatory system of an in utero environment for survival.

By "embryo" or "embryonic" is meant a developing cell mass that has not implanted into the uterine membrane of a maternal host. Hence, the term "embryo" may refer to a fertilized oocyte; an oocyte containing a donor nucleus or cell; a pre-blastocyst stage developing cell mass; or any other developing cell mass that is at a stage of development prior to implantation into the uterine membrane of a maternal host and prior to formation of a genital ridge. An embryo may represent multiple stages of cell development. For example, a one cell embryo can be referred to as a zygote; a solid spherical mass of cells resulting from a cleaved embryo can be referred to as a morula, and an embryo having a blastocoel can be referred to as a blastocyst. An "embryonic cell" is a cell isolated from or contained in an embryo.

By "fetus" is meant a developing cell mass that has implanted into the uterine membrane of a maternal host. A fetus may have defining features such as a genital ridge, which is easily identified by a person of ordinary skill in the art. A "fetal cell" is any cell isolated from or contained in a fetus.

By "mutation" is meant an alteration in a naturally occurring or reference nucleic acid sequence, such as an insertion, deletion, frameshift mutation, silent mutation, nonsense mutation, or missense mutation. Preferably, the amino acid sequence encoded by the nucleic acid sequence has at least one amino acid alteration from a naturally-occurring sequence.

By "substantially identical" is meant having a sequence that is at least 60, 70, 80, 90, or 100% identical to that of another sequence. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

A substantially identical sequence is also one that hybridizes with another sequence under low stringency or high stringency conditions. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci., USA* 72:3961, 1975); Ausubel et al. (*Current Protocols Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

By "treating, stabilizing, or preventing a disease, disorder, or condition" is meant preventing or delaying an initial or subsequent occurrence of a disease, disorder, or condition; increasing the disease-free survival time between the disappearance of a condition and its reoccurrence; stabilizing or reducing an adverse symptom associated with a condition; or inhibiting or stabilizing the progression of a condition. Preferably, at least 20, 40, 60, 80, 90, or 95% of the treated subjects have a complete remission in which all evidence of the disease disappears. In another preferred embodiment, the length of time a patient survives after being diagnosed with a condition and treated with a cell of the invention is at least 20, 40, 60, 80, 100, 200, or even 500% greater than (i) the average amount of time an untreated patient survives or (ii) the average amount of time a patient treated with another therapy survives.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing or stabilizing an adverse symptom associated with a tumor. In one preferred embodiment, the percent of cancerous cells surviving the treatment is at least 20, 40, 60, 80, or 100% lower than the initial number of cancerous cells, as measured using any standard assay. Preferably, the decrease in the number of cancerous cells induced by administration of a cell of the invention is at least 2, 5, 10, 20, or 50-fold greater than the decrease in die number of non-cancerous cells. In yet another preferred embodiment, the number of cancerous cells present after administration of a cell is at least 2, 5, 10, 20, or 50-fold lower than the number of cancerous cells present after administration of a vehicle control. Preferably, the methods of the present invention result in a decrease of 20, 40, 60, 80, or 100% in the size of a tumor as determined using standard methods. Preferably, at least 20, 40, 60, 80, 90, or 95% of the treated subjects have a complete remission in which all evidence of the cancer disappears. Preferably, the cancer does not reappear or reappears after at least 5, 10, 15, or 20 years. In another preferred embodiment, the length of time a patient survives after being diagnosed with cancer and treated with a cell of the invention is at least 20, 40, 60, 80, 100, 200, or even 500% greater than (i) the average amount of time an untreated patient survives or (ii) the average amount of time a patient treated with another therapy survives.

The present invention provides a number of advantages related to the cloning of mammals. For example, the methods decrease the time and labor required to generate genetically modified donor cells which can be used in standard methods to generate cloned or chimeric mammals for medical, research, or agricultural applications. In particular, only small regions of homology from a nucleic acid of interest (e.g., regions that are only 50 nucleotides in length) need to be included in the linear DNA molecule for this molecule to homologously recombine with an artificial chromosome to generate a modified an artificial chromosome with a genetic modification of interest. The presence of a large genomic insert in the artificial chromosome, which is homologous (e.g., at least 90, 92, 96, 98, or 100% identical) to a region of an endogenous chromosome in a cell to be modified, significantly increases the efficiency of homologous recombination between the modified artificial chromosome and the endogenous chromosome and thus reduces the number of transfected cells that need to be screened for the desired homologous recombination event. Due to the relative ease of producing these donor cells, a large number of mammals with different mutations can be generated simultaneously. These methods can be generally applied to introduce any desired genetic modification, such as a knockout modification, conditional knockout modification, knock-in modification, chromosomal deletion, or chromosomal translocation.

Cells that are modified to correct an undesired mutation (e.g., a mutation associated with a disease) can also be rapidly generated for clinical applications. Because the sequence of an endogenous nucleic acid is modified in the cells, these cell transplantation methods may be more effective for long-term expression of the modified nucleic acid than conventional gene therapy techniques, which may be limited by positional effects due to site of integration of a transgene. Moreover, cells that are transplanted into the mammal from which the donor cells were obtained are unlikely to express foreign antigens and thus are unlikely to induce an adverse immune response that results in rejection of the transplanted cells.

Other features and advantages of the invention will be apparent from the following detailed description and from the claims.

BRIEF DESCRIPTION OF THE DRAWINGS

FIG. 5A is a picture of a gel showing the PCR analysis of genomic DNA extracted from clones C38, C52, and C68 and from untargeted ES cells. BAC plasmid DNA (BAC) serves as positive control. PCR fragments from the 5' and 3' ends of the BAC vector and the internal controls are indicated on the left. FIG. 5B is a picture of the FISH analysis of cell lines in FIG. 5A.

FIG. 6A is a picture of a gel showing the PCR analysis of genomic DNA extracted from indicated clones and untargeted ES cells. FIG. 6B is a picture of the FISH analysis of cell lines in FIG. 6A.

FIG. 7A is a picture of gels showing the genotyping of mouse tail genomic DNA by PCR with primers amplifying wild-type (WT) locus and mutant (MT) locus. FIG. 7B is a picture of gels showing the RT-PCR analysis of mRNA extracted from mouse spleenocytes with primers amplifying exons 5 and 6 from fancg/xrcc9, exon 2 from dok3/dok-L, and exon 2 from Iκβras1 to detect the presence of wild-type gene transcripts. Murine β2 microglobulin (for fancg/xrcc9) and caspase 8 mRNAs (for dok3/dok-L and Iκβras1) were used as internal controls.

FIG. 10 is a table illustrating the modification of BACs by homologous recombination in *E. coli*.

FIG. 12A depicts the screening for homologous recombination by PCR and FISH. Broken gray blocks represent large homologous regions; black blocks represent BAC vector sequences. "WT" denotes the wild type locus; "MT" denotes the mutant locus. PCR analysis of genomic DNA extracted from FANCG/XRCC9 targeted ES clones C38, C52, C68, and untargeted ES cells is shown in FIG. 12B. BAC DNA was used as positive control. PCR fragments from the 5' and the 3' of BAC vector and the internal controls are indicated on the left. Blot hybridization of genomic DNA extracted from indicated clones and untargeted ES cells using probes indicated in FIG. 12A and a probe specific for zeo$^r$/neo$^r$ cassette is shown in FIG. 12C.

FIG. 14 is a table summarizing gene-targeting efficiency.

FIG. 17A is a schematic illustrating the sequential insertion of FRT sites into designated introns. FIG. 17B illustrates a FISH analysis of three ES clones. Clones A8 and B6 are the result of homologous recombination events and Clone B4 is the result of a random integration event. FIG. 17C illustrates that all the FRT sites have been faithfully integrated into the ES genome.

DETAILED DESCRIPTION

To overcome difficulties associated with conventional site-specific modification methods, we have developed a method that uses modified artificial chromosomes (e.g., BACs, PACs, or YACs) that contain a genetic modification of interest as targeting constructs. The large amount of sequence that is homologous between the artificial chromosome and an endogenous chromosome of the targeted cells greatly increases the efficiency of homologous recombination between the region of the artificial chromosome containing the genetic modification of interest and the corresponding region of the endogenous chromosome. For example, murine BACs contain 100-150 kilobases of mouse genomic sequence that is substantially identical to an endogenous chromosome of a targeted mouse cell, such as an embryonic stem (ES) cell.

For these methods, an artificial chromosome containing a genomic insert (e.g., a region of a mouse chromosome) with a nucleic acid of interest is obtained from a commercial source or constructed using standard methods. A desired genetic modification is introduced into the nucleic acid of interest in the artificial chromosome by homologous recombination between the artificial chromosome and a linear DNA molecule containing a positive selection marker (e.g., a zeo$^r$/neo$^r$ marker) flanked by two regions of homology to the nucleic acid of interest. In some cases, the desired modification is the insertion of the positive selection marker into the nucleic acid of interest in the artificial chromosome by homologous recombination and the inactivation of the nucleic acid by this insertion. In other cases, one or both regions of homology in the linear DNA molecule have a desired mutation that is introduced into the nucleic acid of interest in the artificial chromosome. If the artificial chromosome is a BAC or PAC, the linear DNA molecule and either the BAC or PAC is introduced into bacteria to allow this homologous recombination to occur. If the artificial chromosome is a YAC, then the homologous recombination is performed in yeast. This method requires very little sequence information about the nucleic acid of interest. For example, homologous regions in the linear DNA fragment as short as 50 nucleotides have been shown to recombine with the corresponding regions in the artificial chromosome to generate the desired modified artificial chromosome. The resulting modified artificial chromosome is introduced into one or more cells (e.g., mouse ES cells), and the genetically modified cells in which homologous recombination occurs between the artificial chromosome and corresponding region of an endogenous chromosome are selected.

Figure 4A:
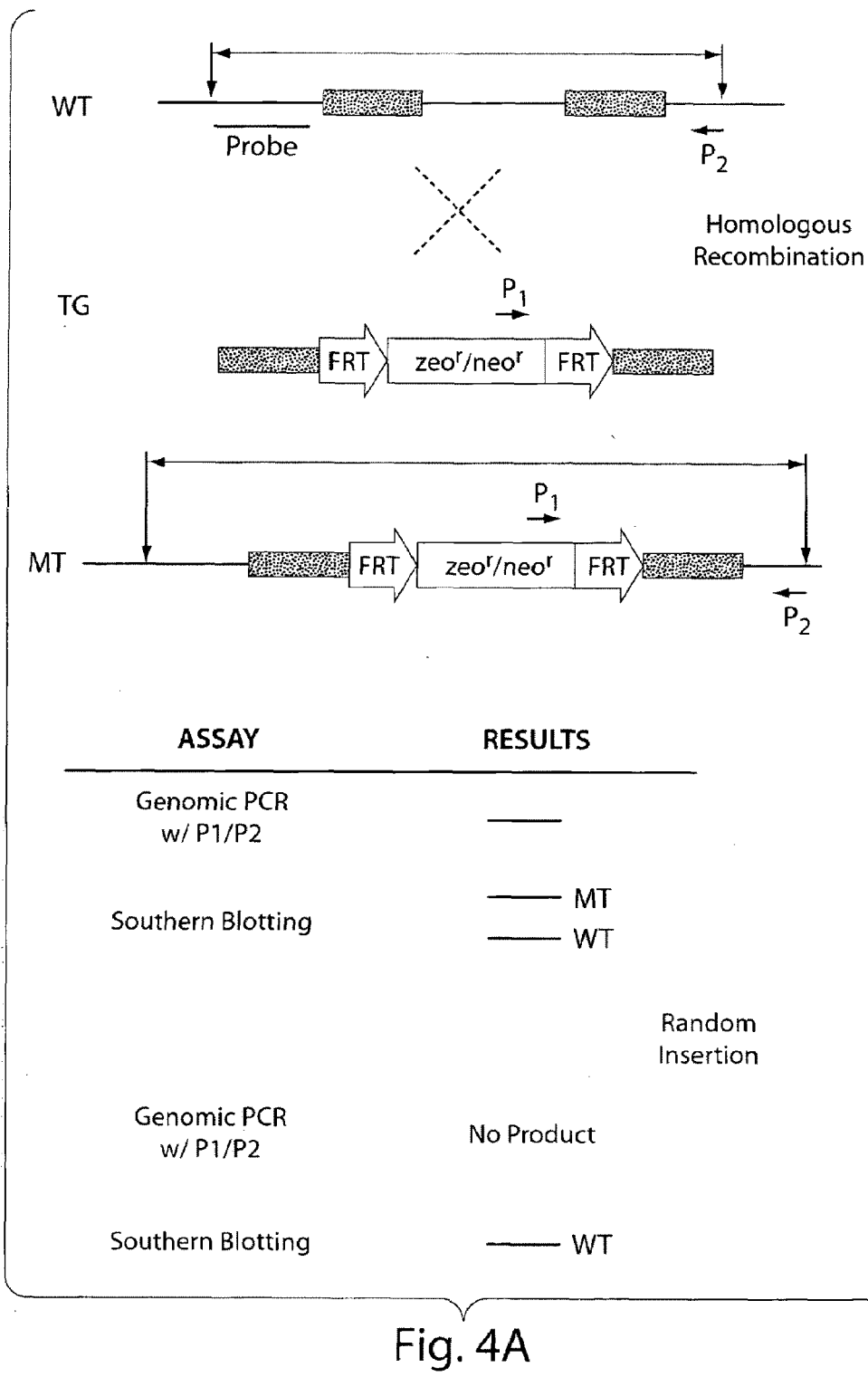
FIGS. 4A-4C are schematic diagrams of strategies for screening targeted ES cells. Homologous recombination can be identified by genomic PCR and DNA blotting when using a conventional targeting construct (FIG. 4A), or by competitive PCR and FISH when using an intact BAC (FIGS. 4B and 4C). Gray blocks represent small homologous regions. Broken gray blocks represent large homologous regions. Black blocks represent BAC vector sequences. Downward arrows indicate restriction endonuclease cleavage sites. "WT" denotes the wild-type locus; "TG" denotes the targeting construct; and "MT" denotes the mutant locus.

Genomic PCR and blotting hybridization are two techniques that have been used in traditional methods to identify homologous recombination in ES cells. Genomic PCR is usually only practical when the flanking region is less then 10 kilobases (FIG. 4A). DNA blot analysis is more reliable but is also limited by the availability of appropriate restriction sites and gel resolution when very large fragments are introduced. Hence, neither method can be applied in general when an entire artificial chromosome is used as a targeting construct in the present methods.

Thus, to use an artificial chromosome (e.g., BAC) for accurate gene replacement in ES or other donor cells, we had to find an effective method to distinguish homologous recombination from random insertion. We solved this problem by determining copy numbers of the target gene locus using fluorescence in situ hybridization (FISH) with the entire artificial chromosome (e.g., BAC) as the probe. This approach allows one to visually distinguish random insertion events, which generate a locus for hybridization, from desired orthotopic targeting events, which maintain the two locus signature of the normal diploid cell. We have observed similar FISH resolution from interphase nuclei and, from metaphase chromosome spreads.

If desired, to reduce the number of FISH experiments that are performed, competitive PCR can be used to detect the vector sequences attached to both ends of the artificial chromosome (e.g., BAC) as a primary screening method to exclude random integration events. We found that most of the BACs remained intact after electroporation into ES cells. In particular, 50% of the G418 resistant colonies usually contained at least one vector end sequence. These clones all showed an extra signal when tested by FISH indicating that random integration had occurred. Because the vector sequences attached to both ends of the BAC are very small and probably are the first to be lost during degradation, as many as 80% of the clones passing the initial PCR screening test can be false positives when detected by FISH. Nonetheless, the frequency of targeting is very high, and the procedure is quite simple.

Figure 12A:
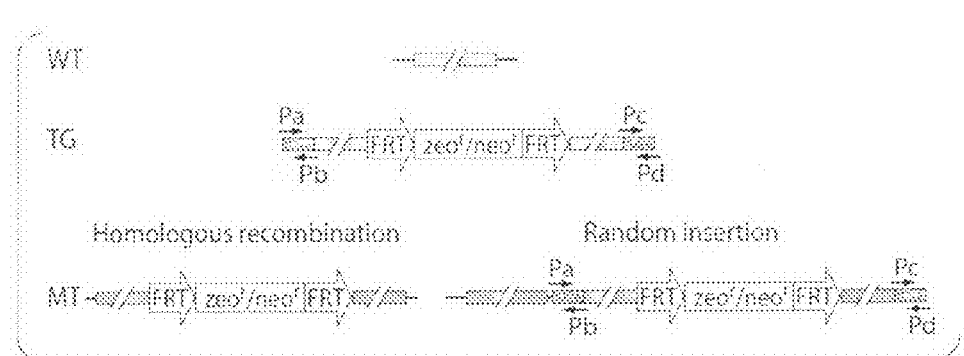
FIGS. 12A-12C illustrate the targeting of ES cells by intact BACs.

An exemplary method for identifying correct targeting events using PCR and FISH is illustrated in FIG. 12A. The BAC is linearized so that flanking vector arms remain on either side of the insert. G418-resistant colonies are first screened for the presence of these arms by PCR, and any colonies containing either of the vector segments are discarded. The remaining colonies are then screened by FISH. If the mutant BAC replaces one of the wild type gene loci, there should be no net gain in gene copy number detected by FISH using the BAC as probe. Alternatively, undesired, random integration should result in the appearance of an additional hybridization signal.

Figure 15:
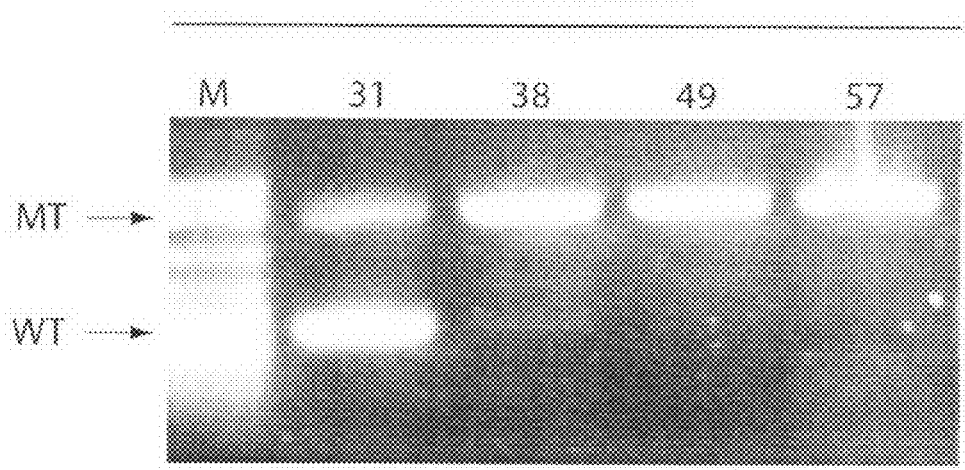
FIG. 15 illustrates a genomic PCR genotyping of Cask-deficient ES clones. Clone 31 shows both the wild type locus (WT) and the BAC (MT) since it is the result of non-homologous integration of the BAC containing the modified cask locus. Clones 38, 49, and 57 are the result of homologous recombination events and only contain the modified locus (MT).
Figure 16:
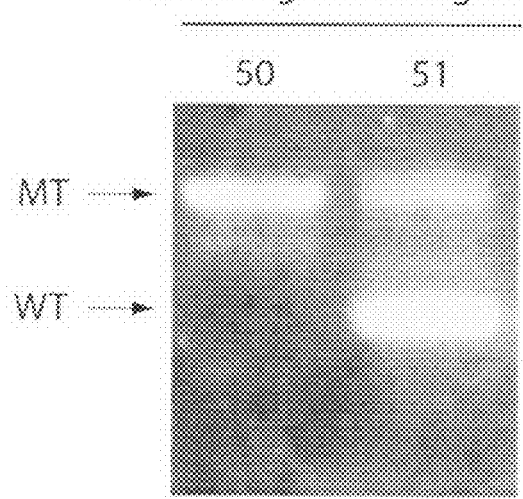
FIG. 16 illustrates a genomic PCR genotyping of maguin-1-deficient ES clones. Clone 51 is the result of non-homologous integration of the BAC containing the modified cask locus and therefore shows both the wild type locus (WT) and the BAC (MT). Clone 50 is the result of homologous recombination events and only contains the modified locus (MT).

Independent knockout mice strains have been derived in which the ES clones passed the FISH screening test, suggesting the generality of the present strategy. In all cases, several positive clones were obtained from only one 96-well plate of colonies, indicating consistent high homologous recombination efficiency in ES cells, probably due to the extensive homology shared between the BAC and the targeted gene locus. We were able to obtain correctly targeted ES clones for four different genes in less than two months. Additionally, less than eight months was required to construct a Fanconi Anemia protein G (FANCG)-containing BAC and to obtain homozygous fancg knockout mice. Four other knockout lines, dok-3, Iκβras1, pag/cbp, and tab2 have also been generated. All of the above five mutant lines have been bred to homozygosity by the above approach. In addition, two X-chromosomal genes, cask and maguin-1 have been targeted and since there is only one copy of them in ES cells, the mutant ES cells are knockout lines as judged by genomic PCR (see FIGS. 15 and 16).

In summary, we have developed a method for rapidly generating genetically modified mammals. It involves two steps: modifying artificial chromosomes in bacteria or yeast via homologous recombination and using the mutant artificial chromosomes to modify ES cells or other cells. We have simplified the identification of orthotopic integration by using FISH with the entire BAC as the probe. To reduce the number of FISH experiments, we used PCR to detect the vector sequences attached to the ends of the BAC as a primary screening method. The system can be used to modify BACs or P1s without the need for special strains or libraries. In fact, the system can be used to modify any artificial chromosome without the need for special strains or libraries (Yu et al., Proc. Natl. Acad. Sci. USA 97:5978-83, 2000 and Zhang et al., Nat. Genet. 30:31-9, 2002). Competitive PCR and FISH are sufficient to screen for homologous recombination events in the cells. The procedure can be streamlined and automated for high-throughput site-specific knockouts production. In principle, it allows several genes to be inactivated simultaneously, which is especially attractive for knocking out families of functionally redundant genes. These methods also provide a simpler and easier solution for more sophisticated genomic manipulations, such as conditional knockouts, knock-ins, and large-scale chromosomal engineering (Ramirez-Solis et al., Nature 378:720-724, 1995 and Smith et al., Oncogene 2002. 21:4521-4529, 1995).

These methods are described further below.

Overview of Present Methods for Generating Genetically Modified Mice

Figure 1A:
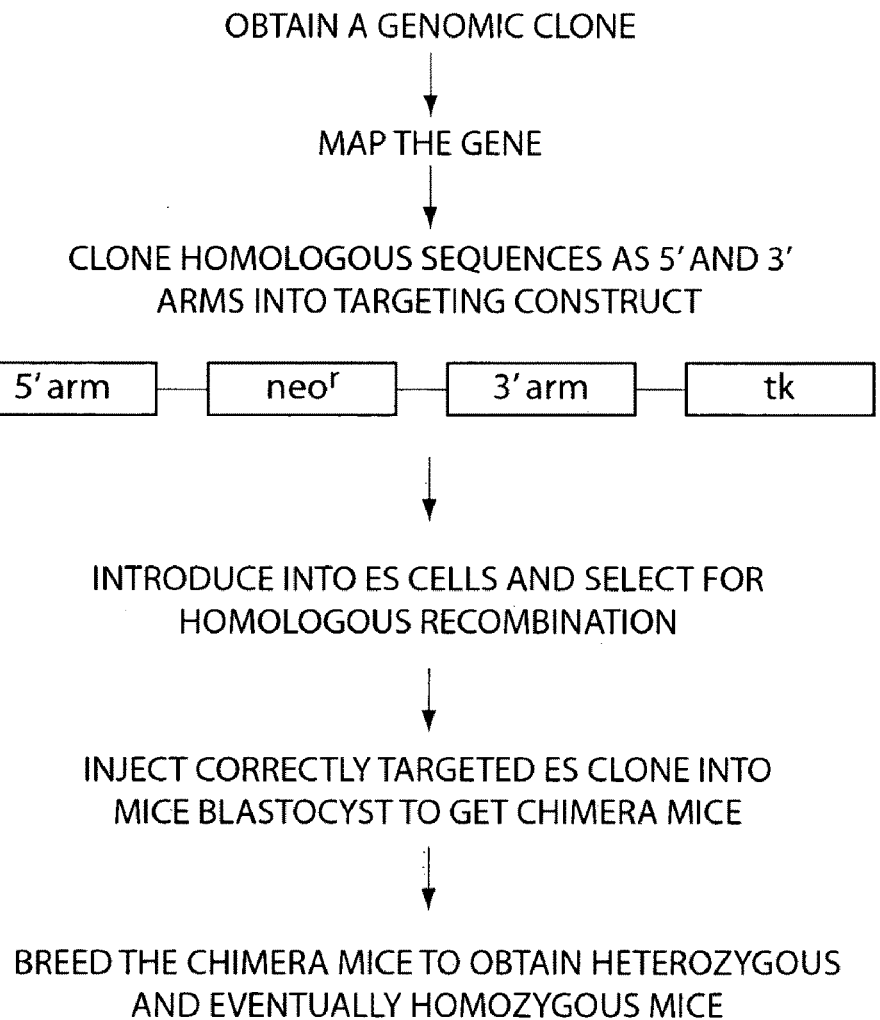
FIG. 1A is a schematic diagram of a traditional method for generating knockout mice.
Figure 1B:
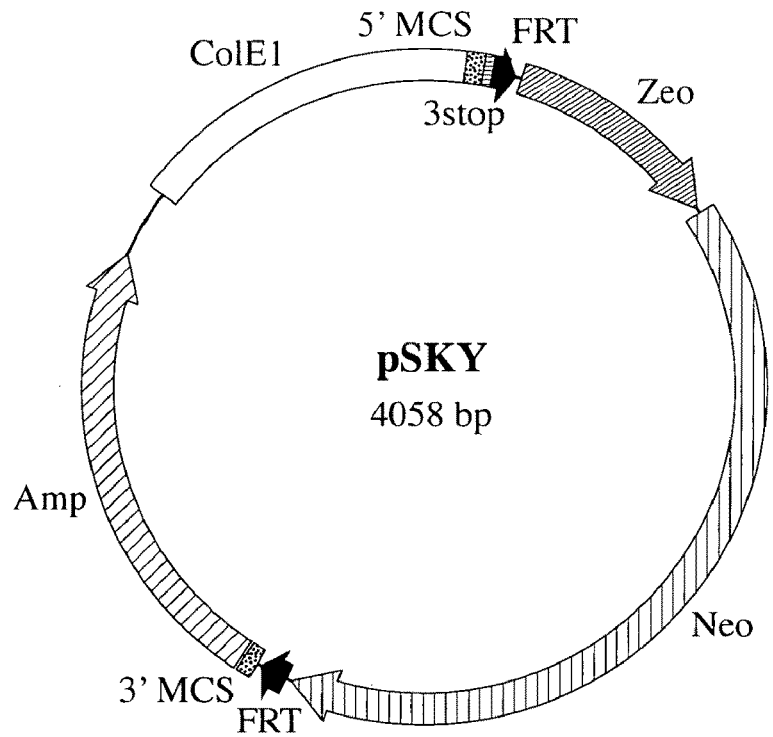
FIGS. 1B and 1C are schematic diagrams of vectors pSKY and pBADλredαβ.

As described above, the present method includes two steps, the modification of an artificial chromosome (e.g., a BAC, PAC, or YAC) in bacteria or yeast and gene targeting in the cells to be modified. The general procedure for generating a modified BAC is illustrated in FIGS. 1D and 1E; similar methods can also be used to generate other modified artificial chromosomes, such as PACs or YACs. In particular, a linear DNA fragment that has an antibiotic resistance gene flanked by two regions of homology to a nucleic acid of interest is transformed into the BAC host. A plasmid that (i) encodes enzymes that mediate homologous recombination between a short linear DNA fragment and a circular plasmid and that (ii) contains a different antibiotic resistance gene than the linear DNA molecule is also transformed into the BAC host, and the expression of the enzymes is induced. Double resistant colonies are screened for homologous recombination events by nested PCR. The DNA is extracted from these colonies and used to transform other bacteria. Cells containing the BAC but not the plasmid encoding the recombinases are selected based on the antibiotic resistance of the transformed cells. Correct targeting events are further confirmed, if desired, by comparing restriction endonuclease digestion and DNA blotting. The resulting modified BAC is isolated, linearized, and transformed into the cells (e.g., ES cells) to be modified.

Figure 4B:
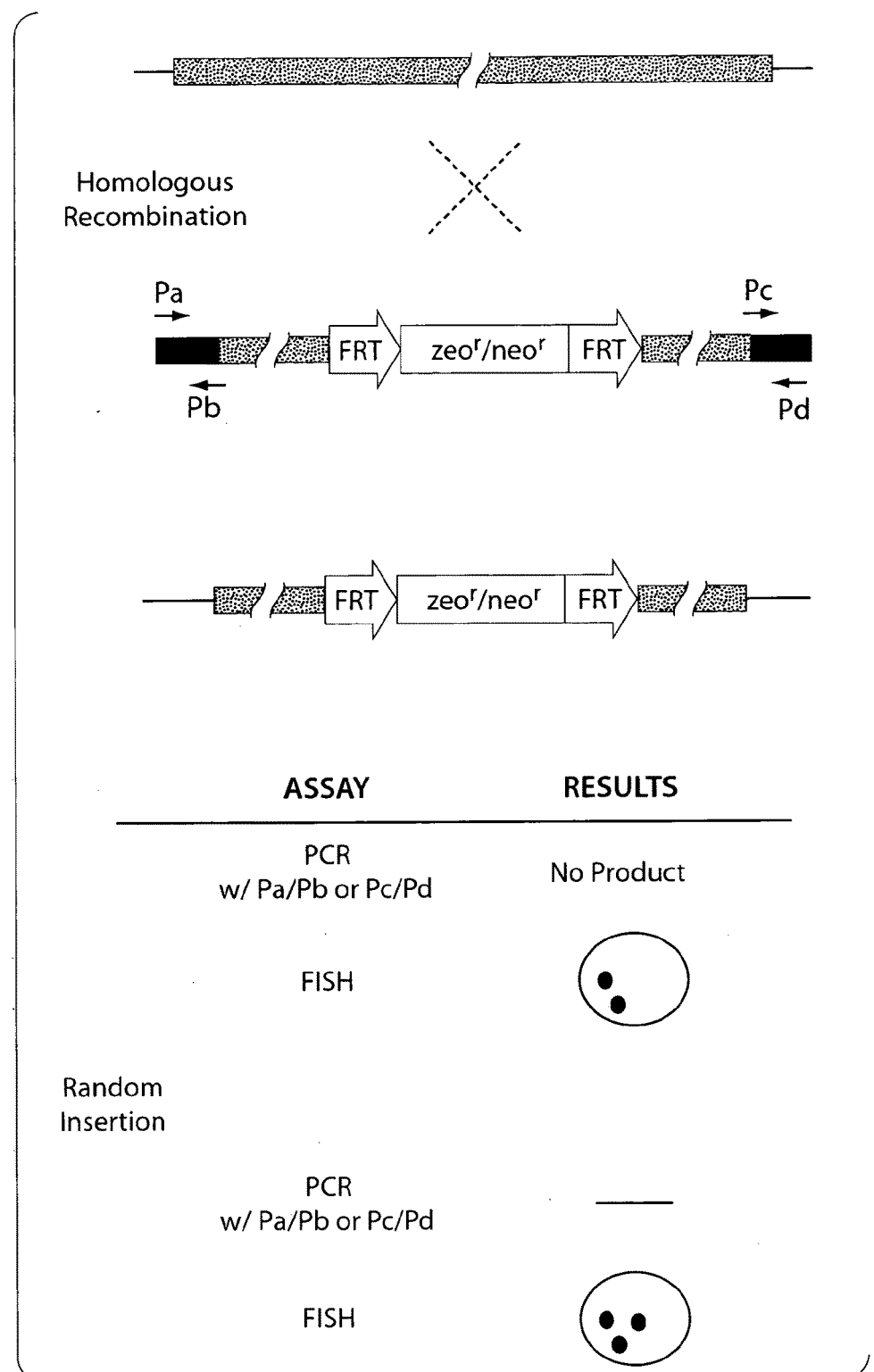
Figure 4C:
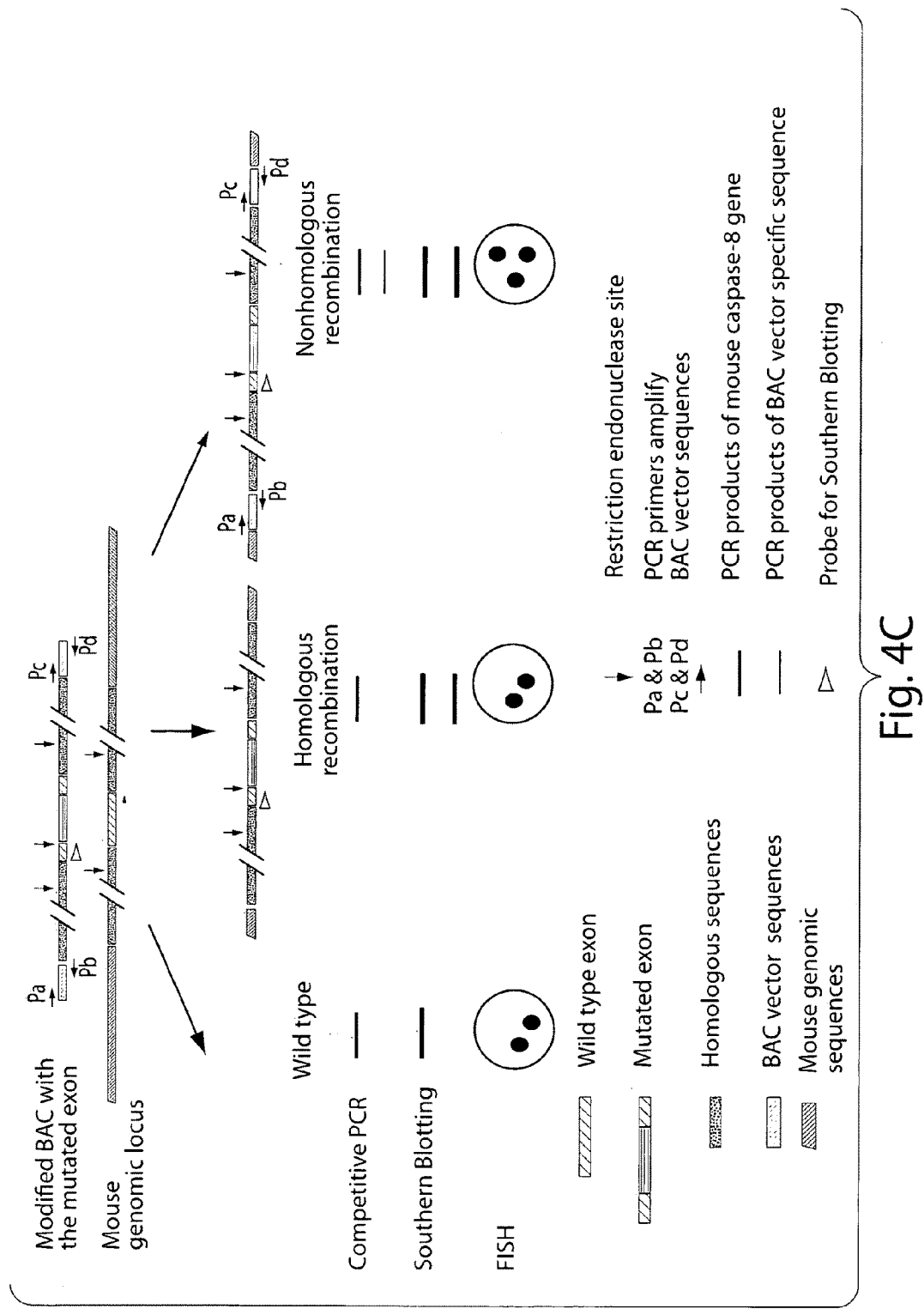

Correct targeting is identified using PCR and fluorescence in situ hybridization. The principle is illustrated in FIGS. 4B and 4C. When the modified BAC is linearized and electroporated into cells (e.g., ES cells), there are two short fragments from the vector attached to both ends. Homologous recombination results in the loss of these sequences, whereas random integration often keeps them intact with the transgene (FIGS. 4B and 4C). Genomic DNA is extracted from resistant colonies (i.e., colonies containing the antibiotic resistant gene from the modified BAC) and subjected to competitive PCR using primers specifically amplifying these fragments along with internal controls primers. Colonies containing either of the vector fragments are discarded (FIGS. 4B and 4C).

Although competitive PCR can exclude random integration events, whether the remaining colonies have undergone homologous recombination is confirmed by FISH. If the modified BAC replaces one of the wild-type gene loci as desired, there should be no net gain in gene copy number detected by FISH using the BAC as probe. On the contrary, random integration results in an additional hybridization spot (FIGS. 4B and 4C).

Generating a Targeting Construct by Modifying a BAC in E. coli

For the generation of a linear DNA fragment containing an antibiotic resistance cassette flanked by two regions of homology, a plasmid designated pSKY was designed to contain a FRT site-flanked dual selection cassette, which includes an E7 promoter-driven zeocin resistant gene (zeo$^r$) for positive; selection in bacteria and a phosphoglycerate kinase (PGK) promoter-driven neo$^r$ for positive selection in ES cells.

In particular, pSKY was constructed using a minimum backbone containing the ColE1 replicon and the ampicillin resistant gene from pBluescript (Stratagene). An E7zeo$^r$ cassette was PCR amplified from pEM7/Zeo (Invitrogen) and ligated 5' to a PGKneo$^r$ cassette from pGT-N28 (NEB) with the PGK polyA signal replace with the SV40 polyA signal and then flanked by FRT sites. Translation stop codons in three reading frames were inserted 5' to the E7zeo$^r$ cassette to terminate any potential translations from upstream. Convenient cloning sites were generated at both 5' and 3' ends. If desired, the zeo$^r$/neo$^r$ cassette can be removed through recombining the flanking FRT sites by the site-specific recombinase Flp (Zhang et al., Nature Genet. 20:123-128, 1998 and Muyrers et al., Nucleic Acids Res. 27:1555-1557, 1999).

A coding region of the gene of interest is identified by PCR amplification of mouse genomic DNA. This region can be as short as, e.g., 130 base pairs. The primer pair amplifying this region (or the PCR product) is used to obtain a mouse genomic BAC clone containing the gene through through the screening service provided by GenomeSystems (now a subsidiary of Incyte Pharmaceuticals). Then, a linear DNA fragment is constructed such that two short regions of homologous sequence from the identified coding region are placed on either side of the zeo$^r$/neo$^r$ cassette in plasmid pSKY (FIG. 1B). In particular, this DNA fragment can be generated by cloning the two regions into the 5' and 3' MCS sites, respectively, in vector pSKY followed by NotI/HindIII digestion. For example, homologous DNA fragments were either generated by PCR amplification or by synthesis and cloned into the 5' EcoRV/EcoRI sites and the 3' BamHI/HindIII sites of pSKY. After sequencing confirmation, the plasmids were digested with NotI/HindIII, and the recombination substrates were gel purified using Qiagen gel extraction kit (Qiagen). Alternatively, the two homologous regions can be tailed to primers amplifying the zeo$^r$/neo$^r$ cassette, and the linear fragment can be obtained by fusion PCR. The homologous regions can be as short as, e.g., 50 nucleotides and can reside on different exons so that the sequences between them are deleted. We have not reached a lower limit on the possible lengths of the regions of homology or an upper limit on the possible lengths separating the two regions.

Figure 1C:
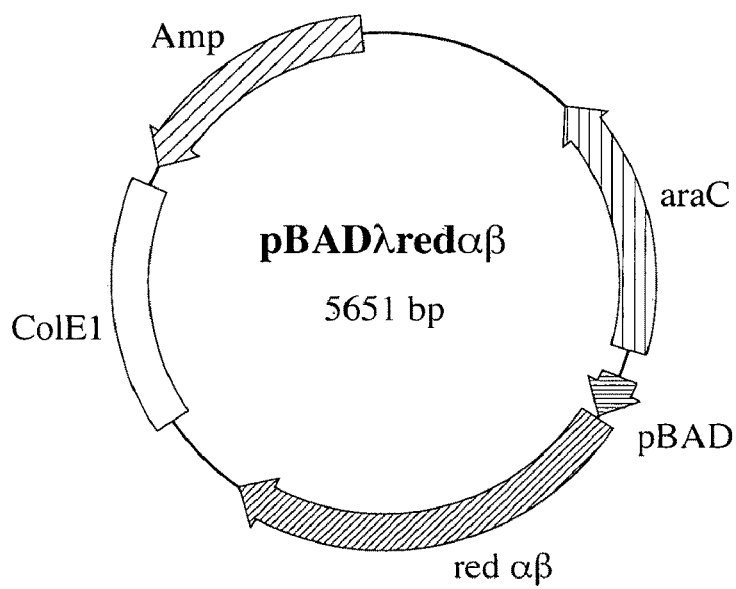
Figure 1D:
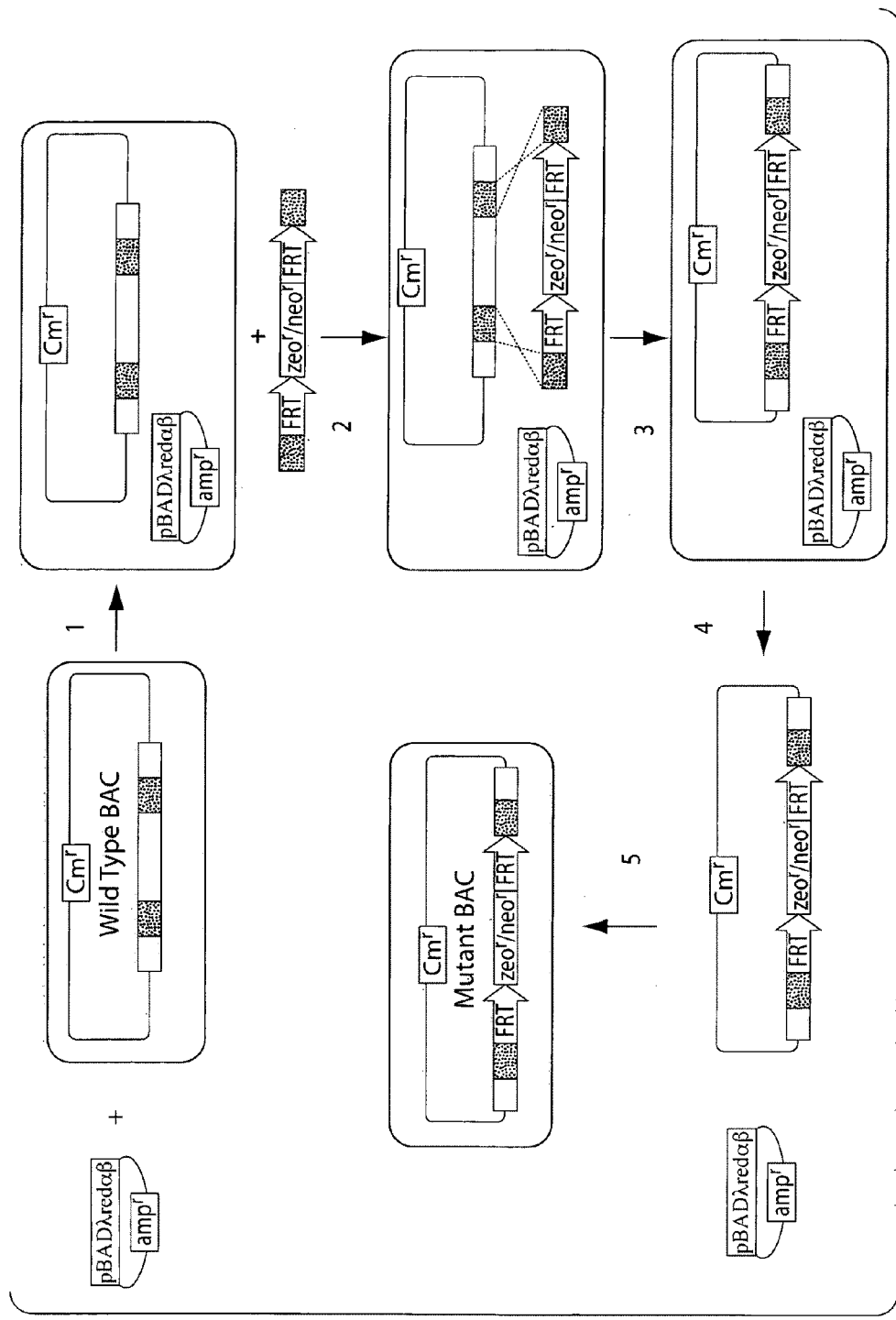
FIGS. 1D and 1E are schematic diagrams of an exemplary procedure for generating a modified BAC. Step 1 involves transforming the pBADλredαβ plasmid into BAC host strain and inducing the expression of αβ genes in the process of making electroporation competent cells. Step 2 involves electroporating the linear substrate and selecting for zeocin/chloramphenicol double resistant colonies. Step 3 involves identifying homologous recombination events by nested PCR, and step 4 involves extracting DNA. Step 5 involves electroporating the mixed DNA into DH10B cells and selecting for chloramphenicol resistant and ampicillin sensitive colonies.
Figure 1E:
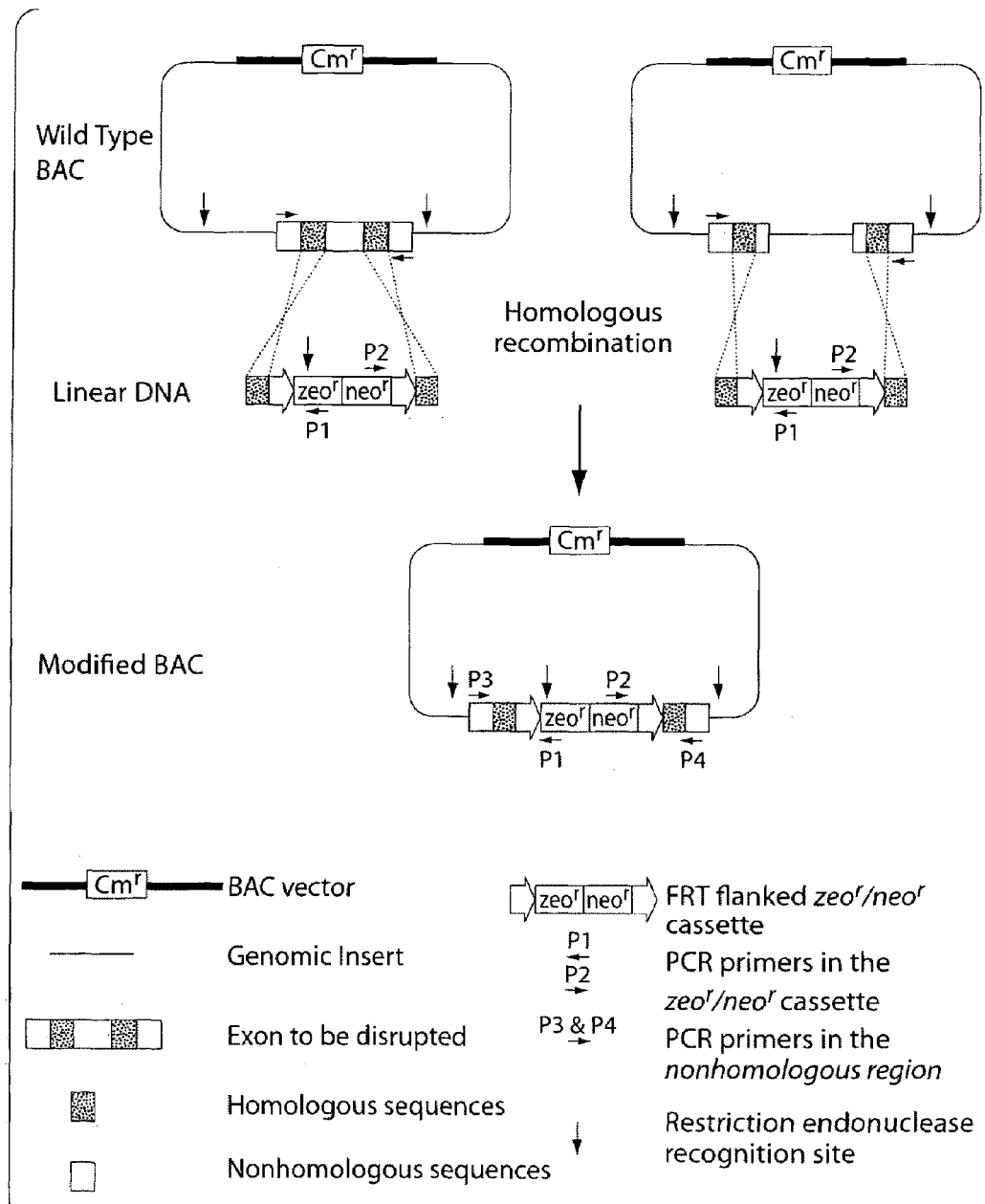

Because the DH10B bacteria strain hosting the BACs are recombination deficient, two shuttle vectors, pBADλredαβ and pBADλredαβγ, were constructed to express a partial or full-length phage λred gene under the control of arabinose-inducible pBAD promoter (FIG. 1C). The λ red gene encodes three subunits and can mediate homologous recombination between a short linear DNA fragment and a circular plasmid (Zhang et al., supra, Muyrers et al., supra, Poteete et al., Virology 134:161-167, 1984). Plasmid pBADλredαβ was also constructed using a minimum backbone containing the ColE1 replicon and the ampicillin resistant gene from pBluescript (Stratagene). The λ redαβ gene was PCR amplified from phage λ DNA and cloned under the pBAD promoter along with the araC regulatory element from pBAD/His A (Invitrogen).

High homologous recombination efficiency was achieved without utilizing the λredγ gene. The λredγ gene encodes Gam, which inhibits the exonuclease activity of the RecBCD complex in E. coli and prevents the linear DNA fragment from degradation. It is possible that the endogenous RecBCD exonuclease does not degrade the linear DNA substrate as quickly as previously believed. Others have previously reported that gain or inhibition of recBC is not required for recombination of linear DNA fragments with the E. coli chromosome. An alternative explanation is that its activity is inhibited in the process of making electroporation-competent cells (Karoui et al., Nucleic Acids Res. 27:1296-1299, 1999).

When the entire λredγ gene including the γ subunit was used, we obtained 50 fold more double resistant colonies; nevertheless, the homologous recombination efficiency dropped 4 fold. Whether λredγ also promotes random insertion is not clear, but high fidelity is desirable when manipulating BAC-sized fragments of DNA because of the need to identify and eliminate clones with unwanted gene rearrangements that occurred during targeting.

The pBADλred shuttle plasmid is transformed into BAC-containing DH10B cells and bacteria resistant to both ampicillin and chloramphenicol are made electroporation-competent after arabinose induction (FIGS. 1D and 1E). The linear DNA fragment described above is electroporated into these cells, and its integration into the BAC renders the cells resistant to zeocin and chloramphenicol (FIG. 1E). The double resistant colonies are screened for correct targeting events by nested PCR using two primers annealing outside the homology regions (P3, P4) paired with two primers annealing within the zeo$^r$/neo$^r$ cassette (P1, P2). A PCR product of the correct length that is amplified by primers P1 and P3 indicates homologous recombination at the 5' end. Similarly, homologous recombination at the 3' end is verified by PCR using primers P2 and P4. The correctly modified BAC is separated from the pBADλredαβ shuttle plasmid by electroporating the mixed DNA into DH10B cells and selecting for colonies resistant to chloramphenical, but sensitive to ampicillin (FIG. 1D).

To determine whether there are any random rearrangements in addition to the desired targeting, the digestion patterns of the wild-type BAC plasmid and the modified BAC plasmid, which contains additional restriction sites due to introduction of the Zeo$^r$/neo$^r$ cassette, are compared (FIG. 1E). Incorporation of the antibiotic resistance cassette can be further confirmed, if desired by DNA Blotting using either the 5' or 3' homology region as a probe.

Targeting of the Wild-type Gene Locus in ES Cells Using the Modified BAC

For the genetic modification of ES cells, the modified BAC DNA is digested by NotI, and the genomic insert with two regions of BAC vector sequence left on both ends is electroporated into the cells. Then, G418-resistant colonies are selected. Genomic DNA of these colonies is extracted and first screened by competitive PCR. Two pairs of primers are designed to amplify the BAC vector DNA left on either end of the linear fragment (Pa & Pb, Pc & Pd, FIGS. 4B and 4C). If homologous recombination occurs, these two regions of BAC DNA are eliminated and not amplified. If random integration occurs, these two regions of BAC DNA remain next to the genomic insert and are amplified by the BAC specific primers. Colonies whose genomic DNA contains the BAC vector specific fragments are discarded. A pair of primers amplifying a larger fragment of mouse caspase-8 gene is used as an internal control in the same PCR reaction.

DNA samples which do not contain the BAC vector specific sequences are subject to DNA Blotting using the same restriction endonucleases and either the 5' or 3' region of homology as a probe (FIGS. 4B and 4C). Although this step cannot distinguish homologous recombination from random integration, this step is used to eliminate any clones with incorrect digestion patterns (FIGS. 4B and 4C). This step can also be used to select the restriction endonucleases and probes which are later used to identify homozygous mutant mice.

A few of the remaining ES clones are analyzed using fluorescent in situ hybridization (FISH) with the whole BAC clone as a probe. If the right locus is targeted, the probe detects two copies of the BAC inserts in the metaphase nucleus in the mutant cells as well as in wild-type, control cells in which no BAC was introduced or in which a control BAC without a knockout cassette was introduced. However, if random integration occurs, more than two copies are detected (FIGS. 4B and 4C). ES clones passing all three tests are injected into mouse blastocyst to make chimeras.

We were not able to demonstrate that one of the gene loci harbors the 1.5 kilobase zeo$^r$/neo$^r$ positive selection marker from the knockout cassette using two-color FISH with the zeo$^r$/neo$^r$ marker as a second probe. We suspect that the zeo$^r$/neo$^r$ marker is too short to be used as a specific probe for FISH. Although the presence of this cassette was not confirmed by two-color FISH, the neomycin resistance of the cells with the inserted BAC indicates that this marker is present. Longer positive selection markers may allow two-color FISH to be used to detect the target gene locus and the positive selection marker simultaneously, if desired.

Generation of Several Modified BACs, and a Modified PAC

To demonstrate that the present methods can be used to modify a variety of nucleic acids, a BAC containing a gene with a known genomic structure (e.g., fancg) and several BACs containing genes with unknown genomic structures were modified with this procedure. As illustrated in FIGS. 2A-2D, 3A, 3B, 8A-8D, and 9A-9D, primer Pzeo and Psv were used to anneal to the antibiotic resistance cassette. Primer Pzeo has the following sequence: 5'-GGC CAG GGT GTT GTC CGG CAC C-3' (SEQ ID NO: 1), and primer Psv has the following sequence: 5'-AAG GTT GGG CTT CGG AAT CG-3' (SEQ ID NO: 2). The primers used for amplifying BAC backbone sequences include Pa: 5'-ACA GAT GCG TAA GGA GAA AAT AC-3' (SEQ ID NO: 3), Pb: 5'-CGC CCT ATA GTG AGT COT ATT AC-3' (SEQ ID NO: 4), Pc: 5'-ATA GTG TCA CCT AAA TAG CTT GG-3' (SEQ ID NO: 5), and Pd: 5'-GGC ACG ACA GGT TTC CCG ACT GG-3' (SEQ ID NO: 6). The primers used for targeting fancg/xrcc9 include G34: 5'-CCG TCT TCC AGC CAC GGA GCG GG-3' (SEQ ID NO:9), G35: 5'-GGC GAT ATC TGC CGT TGG TTC TAA-3' (SEQ ID NO: 10), G36: 5'-CCG AAT TCC AGG CTA CTG GAA A-3' (SEQ ID NO: 11), G37: 5'-CCC GGA TCC CAC CTC CTC TCT AGG-3' (SEQ ID NO: 12), G39: 5'-GGC GAA GCT TTC TGA GCC TTT AGT-3' (SEQ ID NO: 13), G40: 5'-TGG CTA AAT TCA CTA AGT G-3' (SEQ ID NO: 14), Gex5F: 5'-CCT CTG AGG ATC TGC TAC TAC TGC-3' (SEQ ID NO: 15), and Gex6R: 5'-GTG TAC ACC TGG ACT AAC ACG GAC-3' (SEQ ID NO: 16) (Yang et al., Blood 98:3435-3440, 2001). The primers used for targeting Ikbras1 include Ikbras1-1: 5'-gggatggaagactgtgaaacgc-3' (SEQ ID NO: 17), Ikbras1-2: 5'-gtctttgaacftatcaatctc-3' (SEQ ID NO: 18), Ikbras1-3: 5'-aggtggcaatcgttgtgttagg-3' (SEQ ID NO: 19), and Ikbras1-4: 5'-ctggatttgctctgggctgag-3' (SEQ ID NO: 20). The primers used for targeting dok3 include Dok3-1: 5'-gctggcgcaaagtgggctctg-3' (SEQ ID NO: 21), and Dok3-2: 5'-ccgggaaggccagctgacagatg-3' (SEQ ID NO: 22). The primers used for targeting tab2 include: Tab2-1: 5' AATAAC-CTGGATGCCTGCTGCG3' (SEQ ID NO: 25), Tab2-2: 5'GAAGGTTGATAGGCTTGCTGAG3' (SEQ ID NO:26), Tab2-3: 5' TAATCCCATGAACCCTCAGCAAG3' (SEQ ID NO:27), and Tab2-4: 5' GCATCATCAGATCCCATACT-CAG3' (SEQ ID NO:28). Primers for targeting pag/cbp include Pag-1: 5' ATTCTTTCAGAAGACAGCACGCTG3' (SEQ ID NO:29), Pag-2: 5' GCGTCCACCGGTCCCTTCT-GCAG3' (SEQ ID NO: 30), and Pag-3: 5' CGGGTCTTCT-TCCCGAGACTTGTATG3' (SEQ ID NO: 31). Primers for targeting cask include Cask-1: 5'AGGTATTGGAA-GAAATTTC3' (SEQ ID NO: 32), Cask-2: 5'GGCCTTACT-TCAGACTCATG3' (SEQ ID NO: 33), and Cask-3: 5' TTG-GCTCATCCGTGTTCTTTTG3' (SEQ ID NO: 34). Primers for targeting maguin-1 include maguin-1-1: 5'AGGTCT-TGATGACTGTTTGCAG3' (SEQ ID NO: 35), maguin-1-2: 5'CAGTGCACACAAAAGGTCAACTG3' (SEQ ID NO: 36), maguin-1-3: 5' TTATGGCTTAGAAACAGAAATC3' (SEQ ID NO: 37), and maguin-1-4: 5' CCTGTCCAAC-CAAGCAAGAAGACTC3' (SEQ ID NO: 38). Primers for targeting cnk: cnk-1: 5'ATGATGCCCTACAGGACTATC3' (SEQ ID NO: 39), cnk-2: 5'AGGCAAAGCTGCAG-GAACTG3' (SEQ ID NO: 40), and cnk-3: 5' AGGGACATC-CCAGATCTGAG3' (SEQ ID NO: 41). Primers for targeting tim-3 include: Tim-3-1: 5'CTCTGGACTGCC ACTTT-TAAAG3' (SEQ ID NO: 42), Tim-3-2: 5'CCACAAACCT-CATG TCTCAAAG3' (SEQ ID NO: 43), and Tim-3-3: 5'AGCCTTATTACACTGG CCAACTTG3' (SEQ ID NO: 44). Primers for targeting tiap include P1: 5'GTGGT-GACGCCATCATGGGAGCTCCG3' (SEQ ID NO: 45), P2:5' CTCAGCTAATTATCGAG3' (SEQ ID NO:46), and P3: 5' CGGGTTGT CATCGGGTTCCCAG3' (SEQ ID NO:47). Control primers include 5'-GAG GAC ATC TTT CCC TCA GGC-3'(SEQ ID NO: 23) and 5'-CAG AGG CTC TGA GTA AGA CC-3' (SEQ ID NO: 24).

For the preparation of electroporation competent cells, a single BAC clone transformed with pBADλredαβ was grown in 5 ml of LB medium (50 µg/ml ampicillin, 12.5 µg/ml chloramphenicol) until reaching an $OD_{600}$ of 0.6 and diluted into 500 ml of LB medium. The culture was induced with 0.1% L-Arabinose at an $OD_{600}$ of 0.2 and harvested when an $OD_{600}$ of 0.6 was reached. Cells were washed once each with 500 ml of ice-cold dd$H_2O$, 500 ml of ice-cold 0.4 mM HEPES (pH 7.5) solution, and 5 ml ice-cold 15% glycerol. Cell pellet was re-suspended in equal volume of 10% glycerol and stored in −80° C.

For homologous recombination in *E. coli*, a linear DNA fragment (1 to 2 µg) was electroporated into 100 µl of BAC competent cells at 25 µFD, 2.3 kV and 200Ω with a Bio-Rad Gene Pulser. Cells were immediately re-suspended in 1 ml of LB medium and inoculated at 37° C. for 1.5 hours. Transformants were selected on LB plates containing 20 µg/ml zeocin (Invitrogen) and 12.5 µg/ml chloramphenicol (Sigma). Double resistant colonies were screened by standard colony PCR with primers to amplify both the wild-type and mutant locus. The reaction contains 0.2 mM dNTPs, 0.5 µM of primers, and 1 unit of Taq polymerase (Roche) in 20 µl of total volume containing 1× reaction buffer with 1.5 mM $MgCl_2$ (Roche). The cycling conditions were as follows: 94° C. for 3 minutes for 1 cycle; 94° C. for 45 seconds, 55° C. for 45 seconds, and 72° C. for 45 seconds for 30 cycles; 72° C. for 5 minutes for 1 cycle. Reactions were performed on a Stratagene RoboCycler®. Standard restriction digestion and Southern Blotting were performed.

As summarized in FIG. 10, 10 different BACs were modified with an average efficiency of 60% (25% to 100%). The two homologous regions can reside, e.g., in one or two exons and can be as short as, e.g., 50 nucleotides. We have been able to delete up to about 5 kilobases of sequence between the two homologous regions. If desired, even shorter regions of homology or even greater distances between the homologous regions may also be used.

Figure 3A:
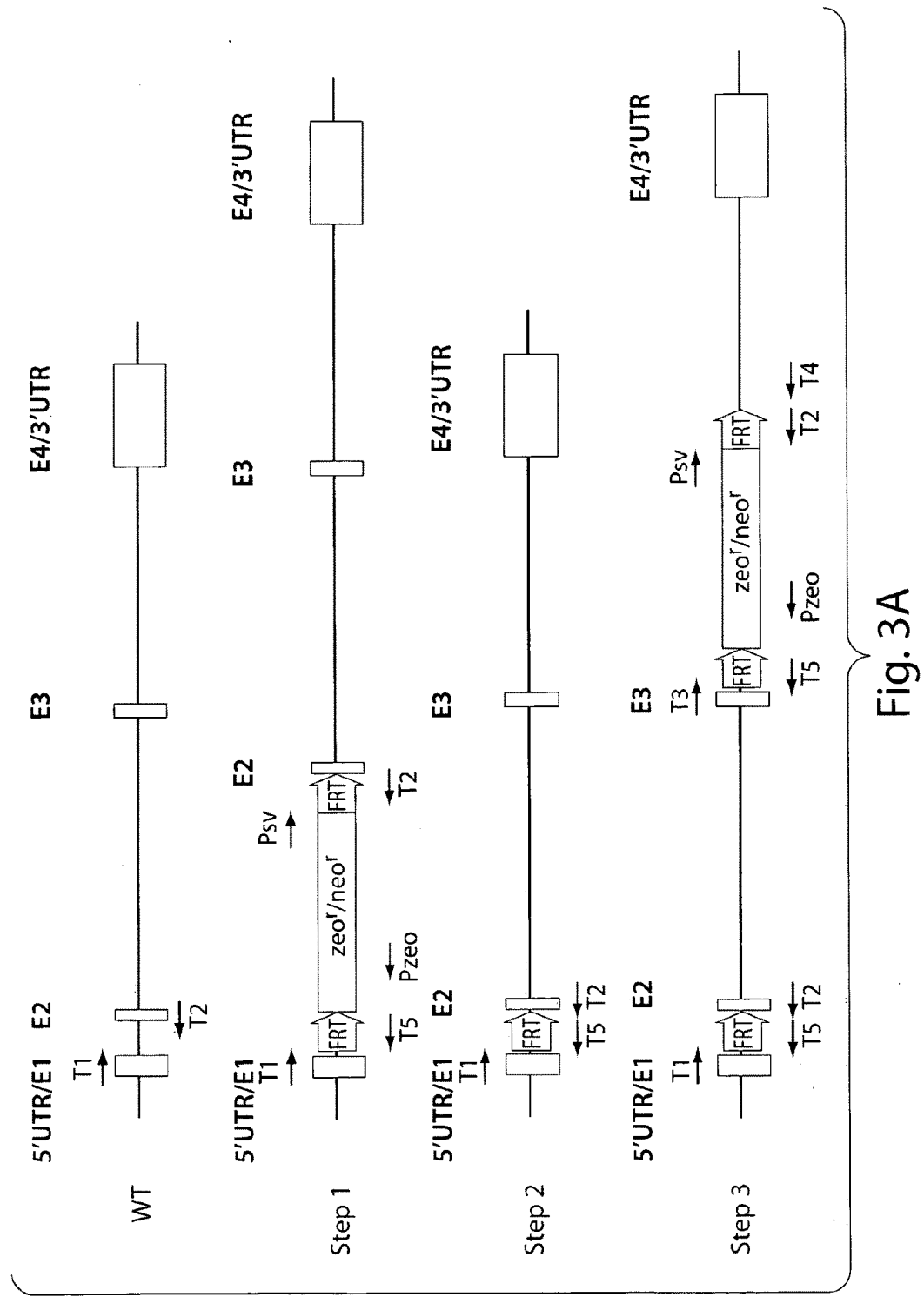
FIG. 3A is a schematic diagram of the generation of a tiap/survine conditional knockout construct that shows the structures of the wild-type gene (WT), intermediate recombinants (Steps 1 and 2), and the final product (Step 3). Open blocks represent exons.
Figure 3B:
FIG. 3B is a picture of a gel verifying homologous recombination by nested PCR. The primers used in each step are indicated on the right.

We have also successfully modified P1 clones with this method. In addition, we have made conditional knockout constructs in three simple steps using a murine P1 clone containing the tiap/survine gene. We first targeted the $zeo^r$/$neo^r$ cassette into intron 1 (step 1, FIG. 3A). We then transduced the homologous recombinants into a Flp expression strain, FLP/DK1. P1 clones with the marker removed were isolated (step 2, FIG. 3A). The $zeo^r$/$neo^r$ cassette was re-introduced into intron 3 (step 3, FIG. 3A). Products in each step were verified by nested PCR (FIG. 3B).

Generation of fancg/xrcc9 Knockout Mice

Figure 2A:
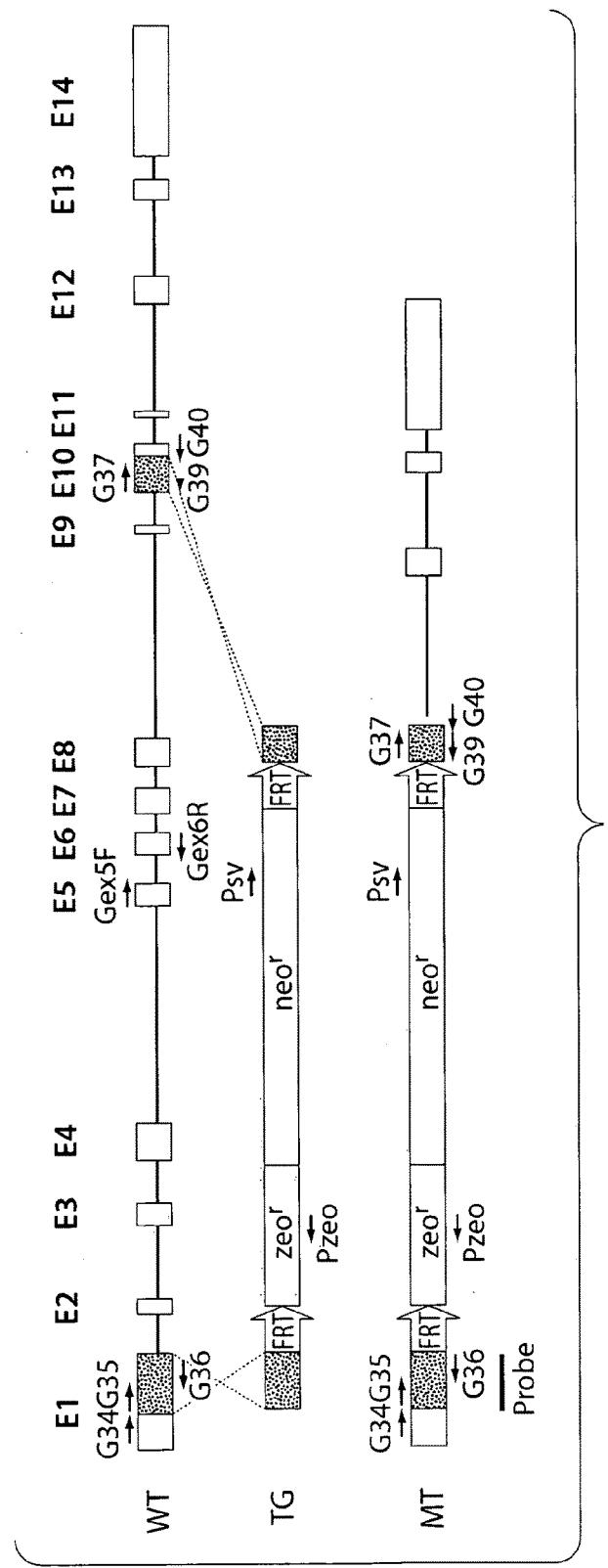
FIG. 2A is a schematic diagram of the generation of a fancg/xrcc9 knockout construct that illustrates the structures of the wild-type gene (WT), the linear substrate (TG), and the mutant gene (MT). The black blocks represent homologous sequences. The open blocks represent exons.
Figure 2B:
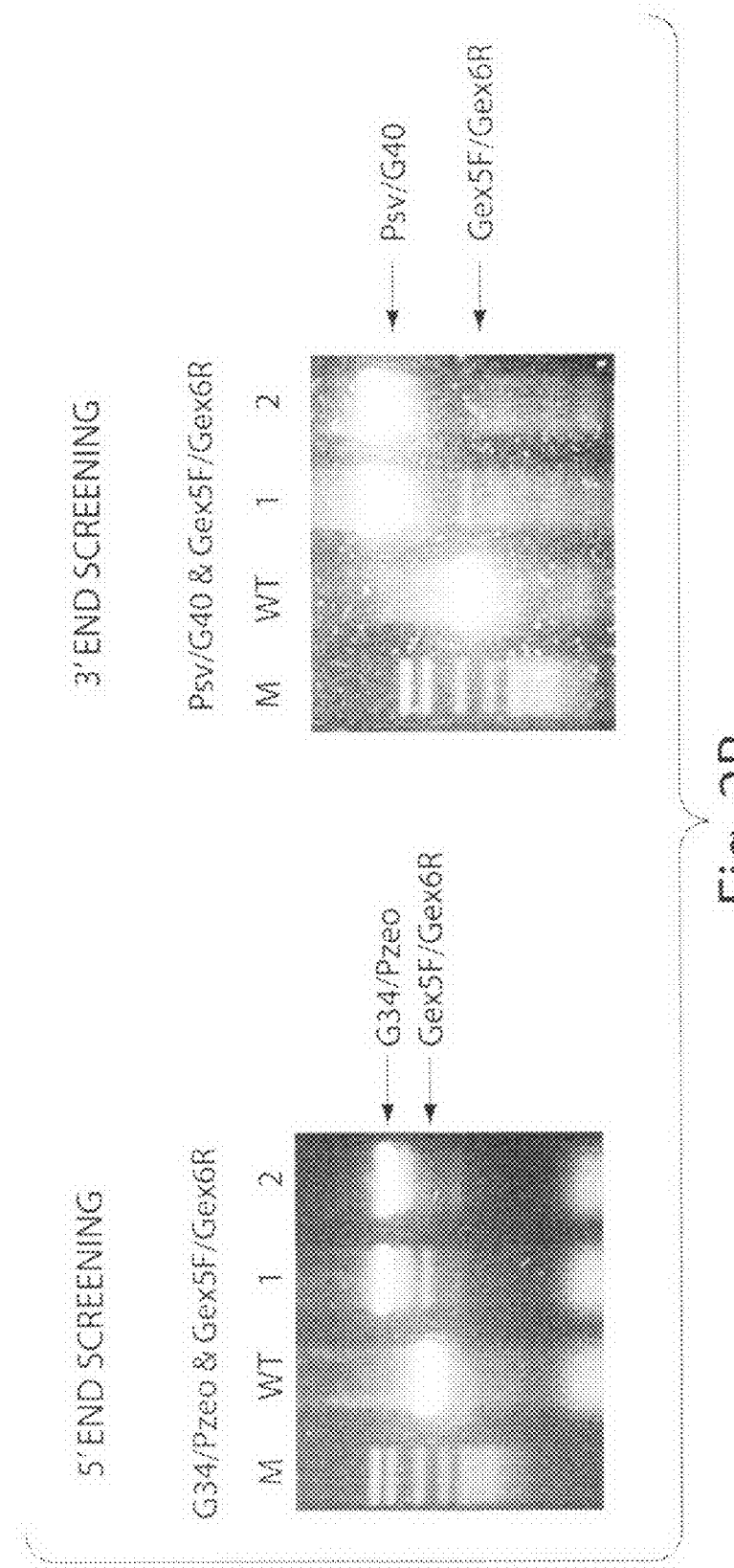
FIG. 2B are pictures of gels of nested PCR reaction mixtures that show correct integration at 5' and 3' sites and deletion of exons 5 and 6.
Figure 11A:
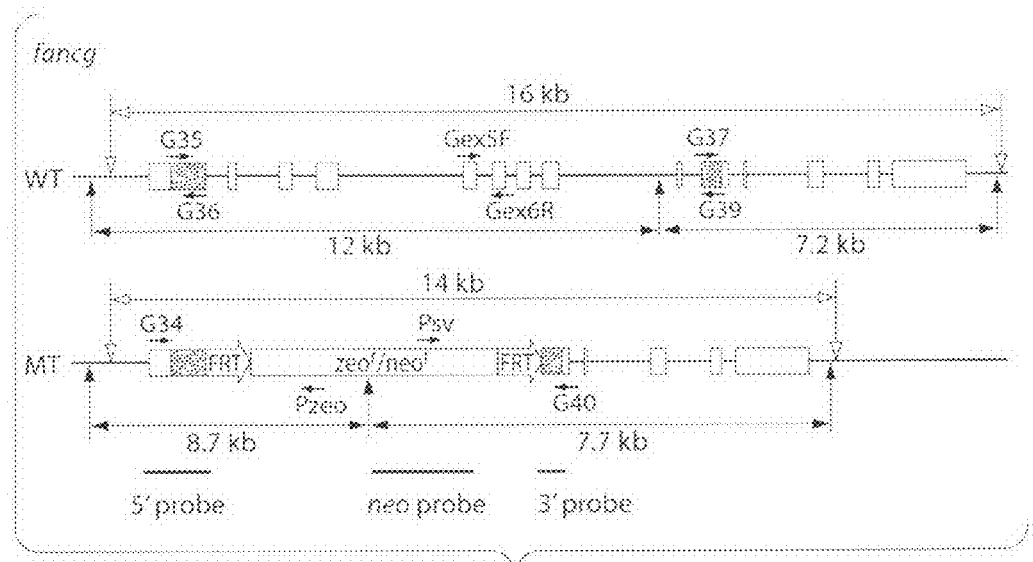
FIGS. 11A and 11B illustrate the generation of the fancg/xrcc9 knockout construct. The structures of the wild type gene (WT) and the mutant gene (MT) are depicted in FIG. 11A. Gray blocks represent homologous sequences; open blocks represent exons. Black arrows are SpeI sites; open arrows are EcoRV sites. PCR results using primers indicated in FIG. 11A show correct integration at the 5' and the 3' sites and deletion of exons 5 and 6 (FIG. 11B).
Figure 11B:
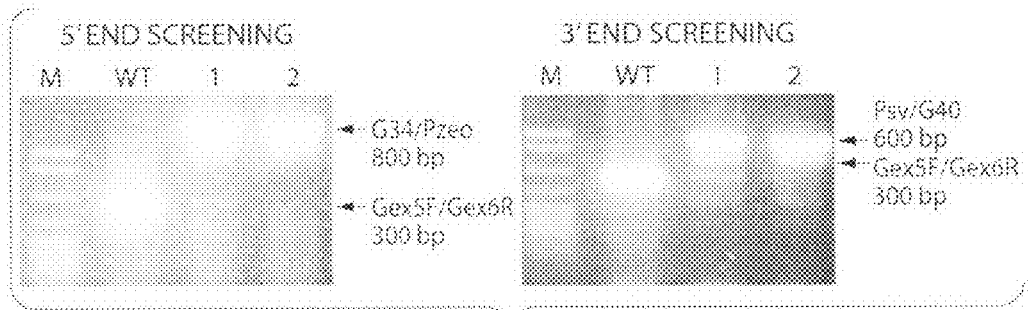

As described above, the $zeo^r$/$neo^r$ cassette was introduced into a BAC clone containing the murine fancg/xrcc9 gene. The marker replaced exons 1 to 10 with 480 nucleotides and 260 nucleotides of homologous sequences from exons 1 and 10, respectively (FIGS. 2A and 11A). Two primers outside the homologous regions (G34 and G40) paired with two primers inside the $zeo^r$/$neo^r$ cassette (Pzeo and Psv) were used to screen double resistant colonies for correct targeting events at the 5' and 3' end, respectively, by nested PCR (FIGS. 2B and 11B). Among 24 colonies picked, all produced predicted PCR fragments at both ends. In addition, the PCR product amplified from exons 5 and 6 was only observed in the wild type BAC, suggesting these exons were deleted in the modified BACs (FIG. 2B).

Figure 2C:
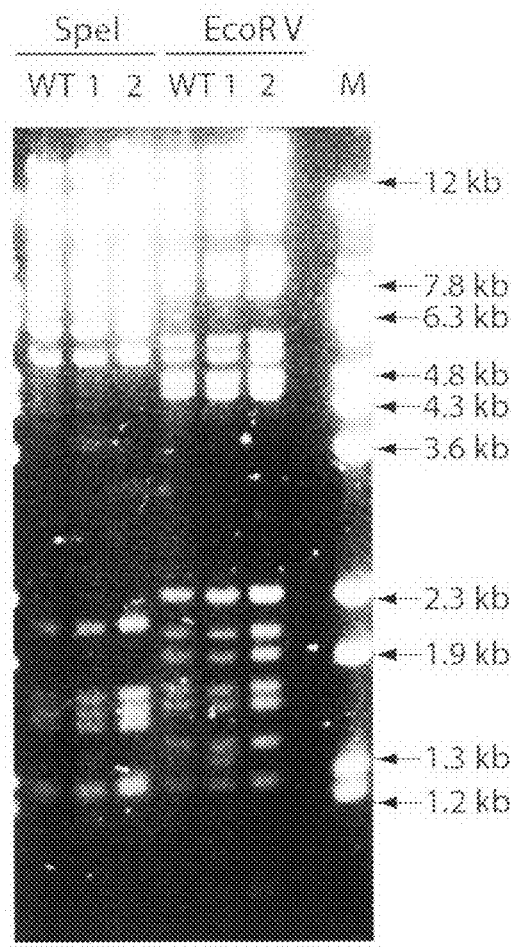
FIG. 2C is a picture of a gel of a restriction digestion of DNA from wild-type (WT) and two modified BACs (1 & 2) by SpeI and EcoRV.
Figure 2D:
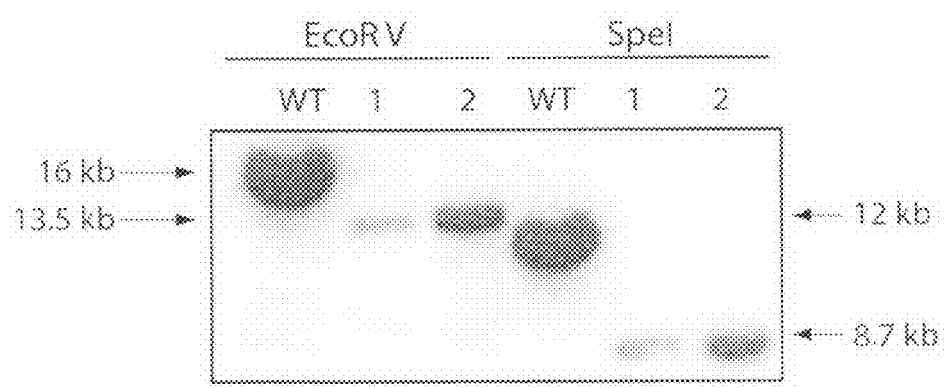
FIG. 2D is a picture of a DNA blot of the gel in FIG. 2C with the probe indicated in FIG. 2A.

To determine whether any unintended rearrangements were generated during modification, the digestion patterns of EcoRV (i.e., a restriction site that is absent in the linear DNA fragment) or SpeI (i.e., a restriction site that is unique in the linear DNA fragment) restriction sites of two independent modified BACs were compared with those of the wild-type BAC. No gross rearrangements were detected in the modified BACs. (FIG. 2C). DNA blotting using the 5' homologous region as probe demonstrated that there was a single copy of the marker integrated at the desired site (FIG. 2D). The fidelity of this procedure was further confirmed by shotgun sequencing of the modified BAC.

This modified BAC was used to target the fancg/xrcc9 locus in ES cells. In particular, BAC DNA was purified using a Qiagen Large-Construct kit, linearized by NotI digestion, extracted once using phenol:$CHCl_3$, precipitated, and resuspended in 0.1×TE buffer (pH 8.0) at 1 µg/µl. ES cells were cultured according to standard conditions (DePamphilis, ed. Methods in Enzymology, Vol. 225 Academic press, Inc., 1993), and 6×10$^6$ ES cells were electroporated with 30 µg of BAC DNA at 0.23 kV, 960 µFD by a Bio-Rad Gene Pulser. Selection was started the second day after transfection with medium containing 400 µg/ml G418 (Invitrogen/Gibco). Colonies were-picked into 96-well plates Genomic DNA was extracted according to standard protocols (DePamphilis, supra). About 0.1 µg of genomic DNA was used as templates in competitive genomic PCR. Cycling conditions were the same as described above. The control primers for competitive PCR include forward: 5'-GAG GAC ATC TTT CCC TCA GGC-3' (SEQ ID NO: 7), and reverse: 5'-CAG AGG CTC TGA GTA AGA CC-3' (SEQ ID NO: 8).

Figure 5A:
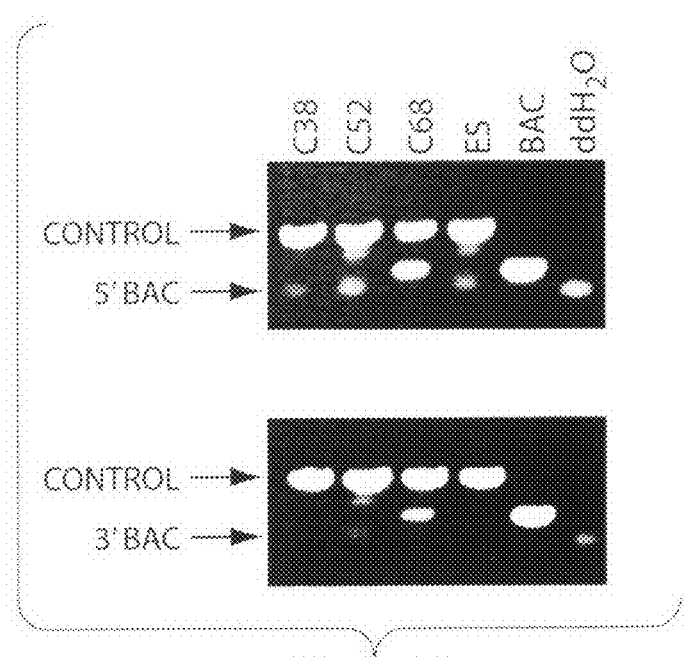
FIGS. 5A and 5B illustrate the identification of fancg/xrcc9-targeted ES cells.
Figure 12B:
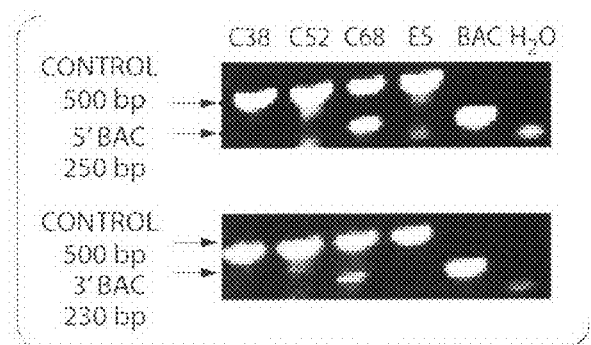

Among 96 PCR reactions, 38 showed both the control PCR fragment and the BAC vector fragment (e.g., C68 in FIGS. 5A and 12B), 22 showed only the control PCR fragment (e.g., C38 and C52, FIGS. 5A and 12B) and 36 showed neither. We performed FISH on clones C38, C52, and C68 along with the wild type ES cells using the entire BAC as probe. For this analysis, standard FISH procedures were applied with minor modifications. For staining interphase nuclei, about 10$^5$ cells were either directly seeded on a 10-well slide (Fisher) or on a regular slide (Fisher) by spinning in a Cytospin centrifuge. Slides were air-dried briefly and fixed in freshly made 4% paraformadehyde in PBS (pH 7.4) for 10 minutes at room temperature. After rinsing off the excess fixative in PBS, the slides were stored in 70% ethanol at 4° C. For staining metaphase spread chromosomes, the cells were treated, and the slides were prepared according to standard procedures. Either random priming (Prime-It® Fluor Fluorescence Labeling Kit, Stratagene, LaJolla, Calif.) or nick-translation (BioNick DNA labeling system, Invitrogen/Gibco) worked well for labeling BACs. Under the condition we used, random priming yielded stronger signals. Manufacturers' protocols were followed and 35 µg COT-1 DNA (Invitrogen/Gibco) were usually used to suppress nonspecific signals. The probe was dissolved in Hybrisol VI (Ventana, Tucson, Ariz.) and then denatured at 75° C. for 10 minutes followed by incubation at 42° C. for 1 hour. Slides seeded with 10$^5$ cells per sample were fixed in 4% (wt/vol) paraformadehyde in PBS (pH 7.4) for 10 minutes at room temperature. Slides were then dehydrated two minutes each in 80%, 85%, 95%, and 100% ethanol. After air-drying, slides were then denatured in 70% (vol/vol) deionized formamide (American Bioanalytical, Natick Mass.), 2×SSC (pH 7.0) at 72° C. for 10 minutes and dehydrated through ice-cold 70%, 80%, 95%, and 100% ethanol. The probe was adjusted to 10 ng/µl, and 4 µl was applied per sample area. Hybridization was carried overnight in a humid chamber at 42° C. Slides were washed three times in 2×SSC (pH 7.4) at 72° C. for 7 minutes each and once in 0.2×SSC (pH 7.4) at 72° C. for 7 minutes. Signals were then amplified using TSA™ Fluorescence Systems (NEN™ Life Science Products, Boston, Mass.) following the manufacturer's protocol. Slides were finally counterstained with DAPI in 4×SSC, mounted in Vectashield (Vector Laboratories, Inc., Burligame, Calif.), and observed under a Zeiss Axioplan 2 fluorescence microscope.

Figure 5B:
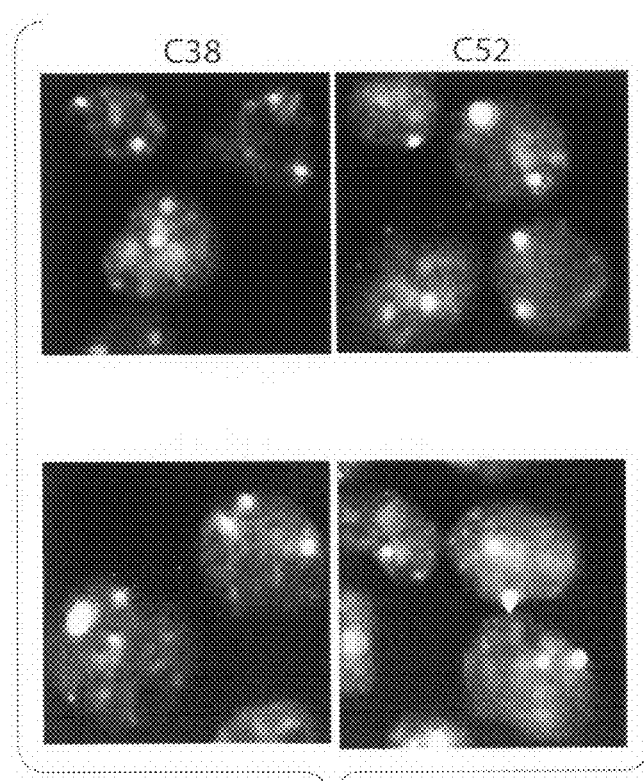

Using this FISH analysis, we detected two signals in clones C38 and C52 as well as in the untargeted ES cells (FIG. 5B) and an extra signal in clone C68 (FIG. 5B), suggesting that C38 and C52 were correct targeting products and C68 was the result of random integration.

Figure 12C:
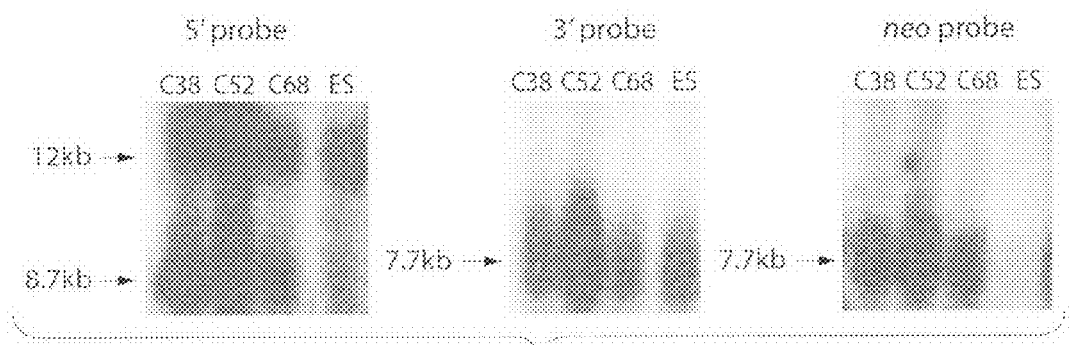

Although TSA-FISH has been previously reported to be reliable for the detection of less than 10 kb regions, genomic DNA hybridization was also performed to exclude the possibility that G418 resistance could be ascribed to the random integration of a zeo/neo fragment that is too small to be detected by TSA-FISH (FIG. 12C). The expected patterns were found with all three probes, indicating that the $zeo^r/neo^r$ marker had integrated into the fancg/xrcc9 locus and that the 20 kb surrounding genomic region had not undergone any disruption other than the desired targeting event (FIG. 12C). As expected, DNA hybridization alone could not distinguish orthotopic (C38 and C52) from ectopic (C68) integration events (FIG. 12C). We estimate that the region encompassed by the blotting data represents $\frac{1}{5}$ to $\frac{1}{7}$ of the intact BAC. Although large DNAs are known to be susceptible to breakage by hydrodynamic shear, the protocol used here minimizes the manipulation of the BAC DNA in vitro and to date no evidence of adventitious rearrangement of the targeting site has been observed. Consistent with this result, it has been previously reported by others that cells modified by gene targeting with one DNA fragment rarely simultaneously incorporate a second DNA fragment.

Figure 7A:
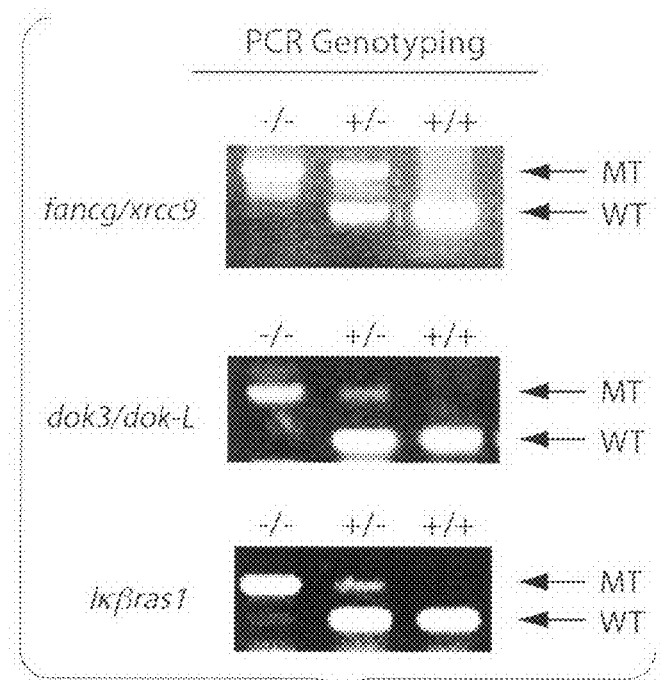
FIGS. 7A and 7B illustrate the generation of knockout mice.
Figure 7B:
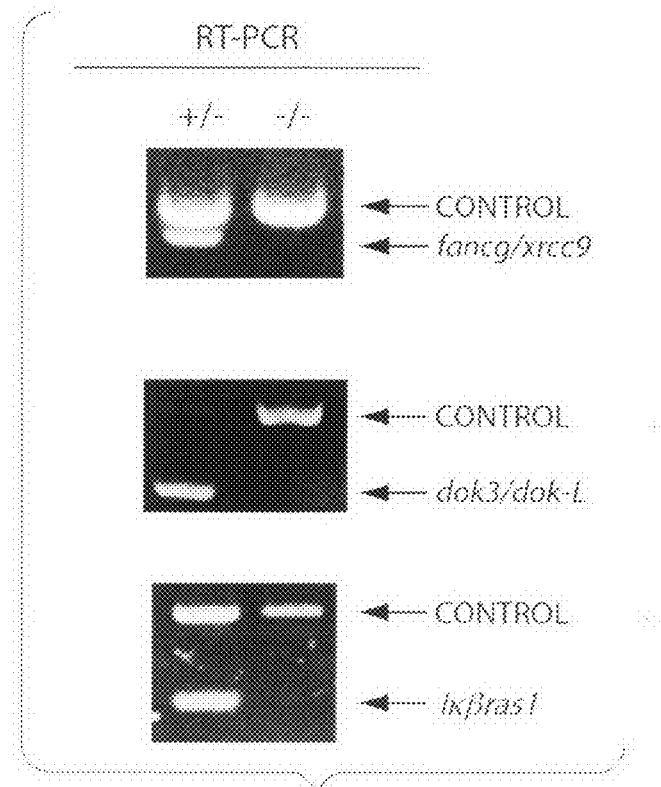
Figure 8A:
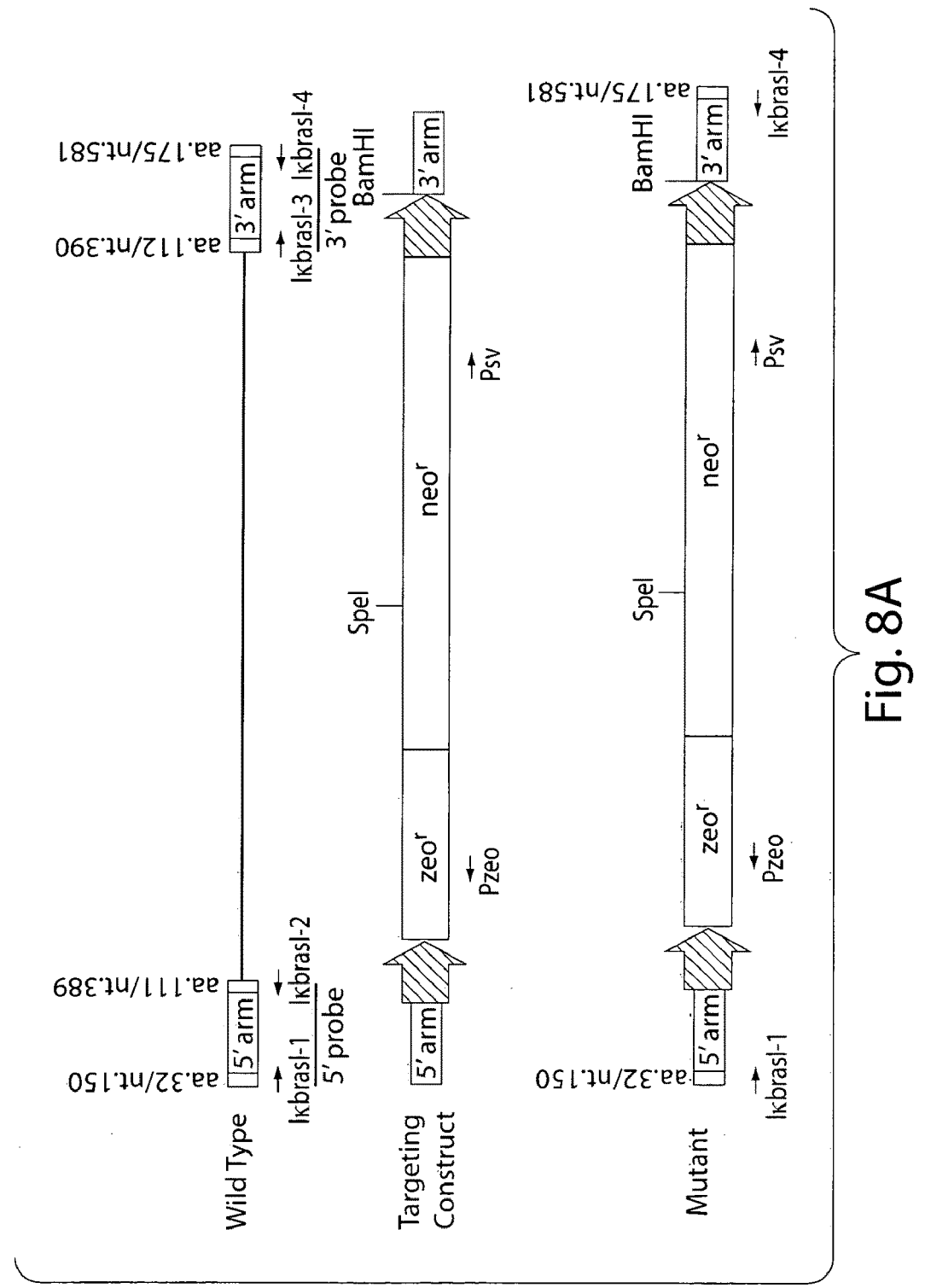
FIG. 8A is a schematic diagram of the generation of a Iκβras1knockout construct that illustrates the structures of the wild-type gene (WT), the linear substrate (TG), and the mutant gene (MT). The homologous sequences are labeled as 5' arm and 3' arm. The hatched arrows are FRT sites. The open blocks represent exons.
Figure 8B:
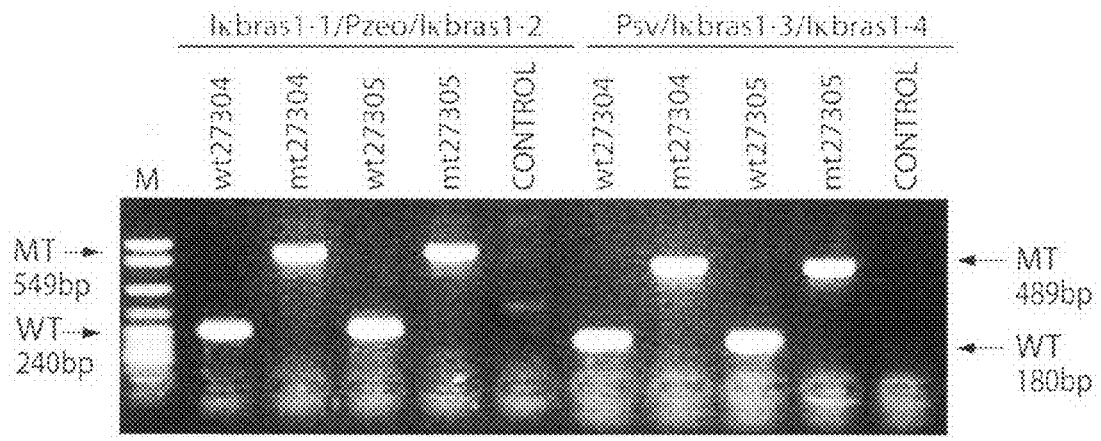
FIG. 8B is a picture of a gel of nested PCR reaction mixtures that show correct integration at of the 5' and 3'ends of the antibiotic resistance cassette.
Figure 8C:
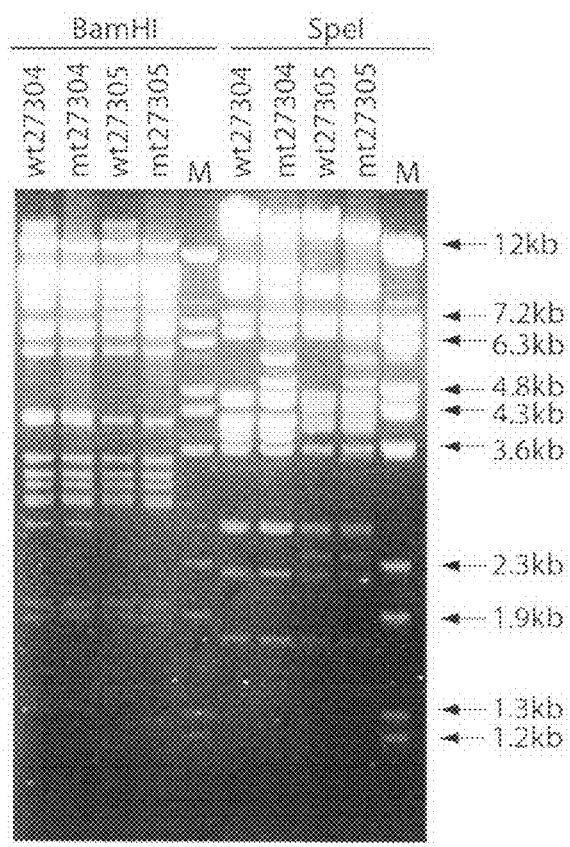
FIG. 8C is a picture of a gel of a restriction digestion of DNA from wild-type (WT) and modified BACs.
Figure 8D:
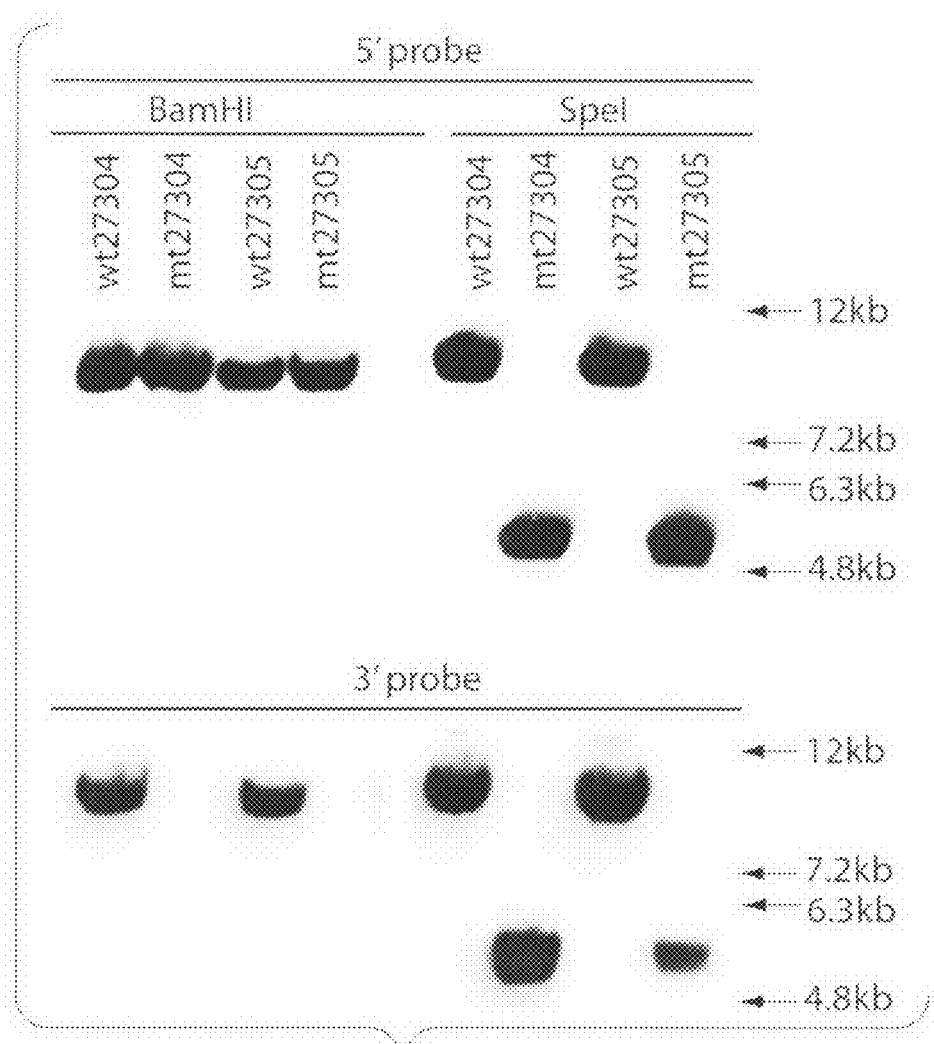
FIG. 8D is a picture of a DNA blot of the gel in FIG. 8C with the probes indicated in FIG. 8A.
Figure 9A:
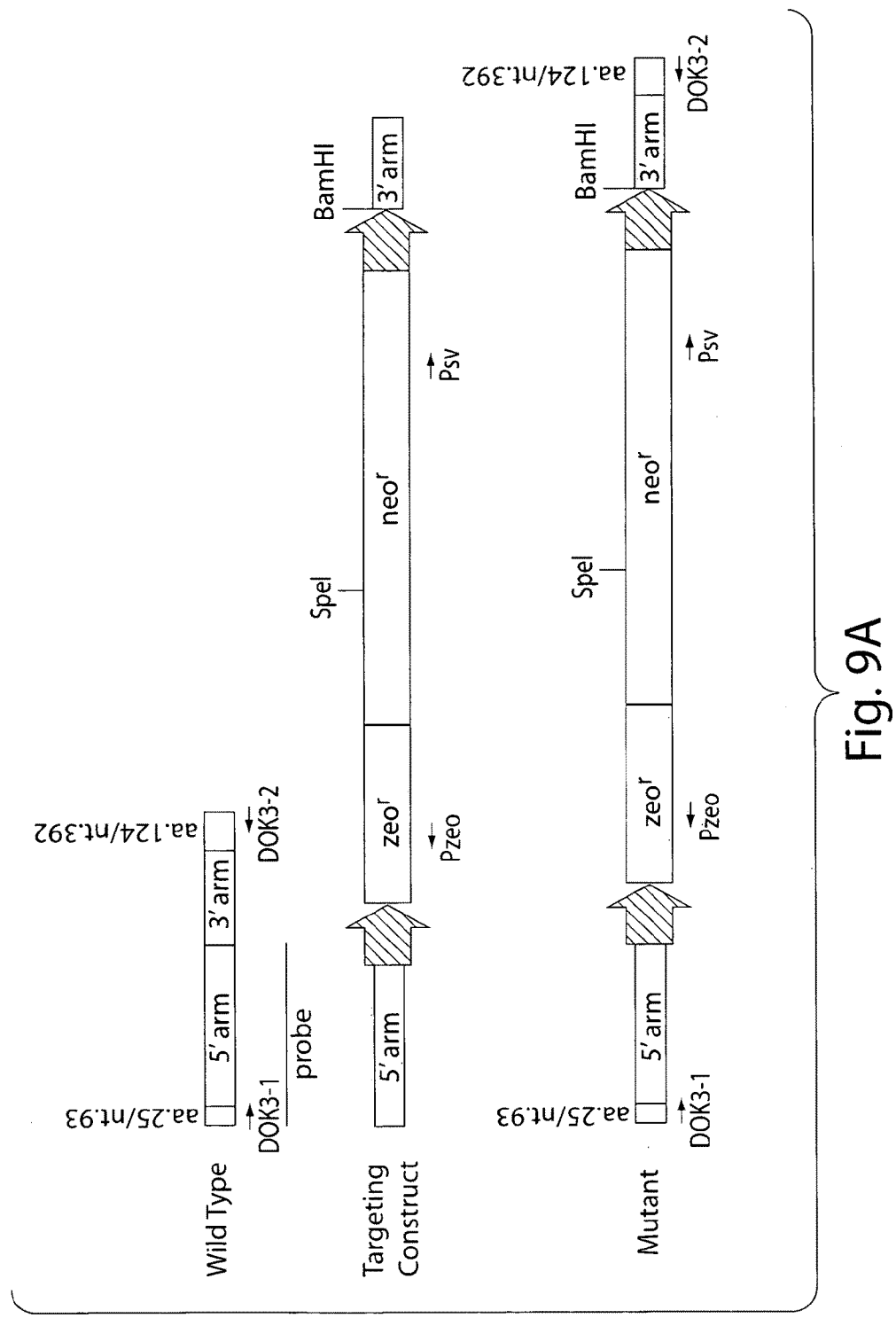
FIG. 9A is a schematic diagram of the generation of a dok3 knockout construct that illustrates the structures of the wild-type gene (WT), the linear substrate (TG), and the mutant gene (MT). The homologous sequences are labeled as 5' arm and 3' arm. The hatched arrows are FRT sites. The open blocks represent exons.
Figure 9B:
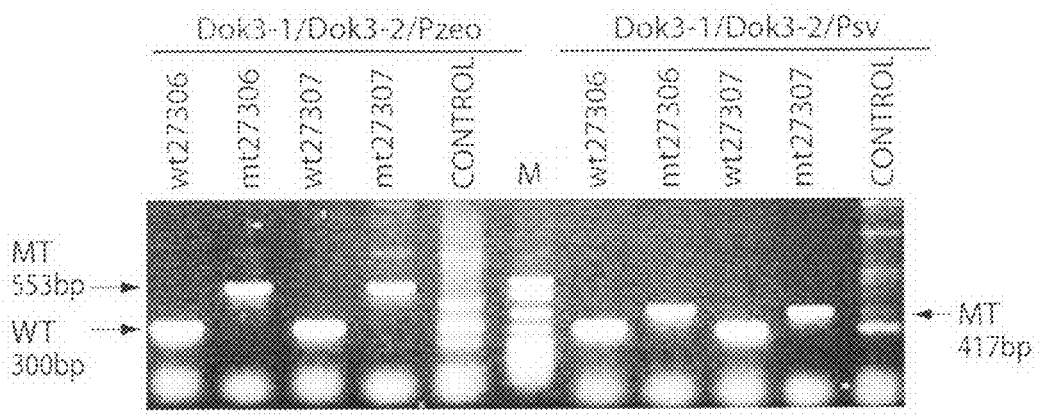
FIG. 9B is a picture of a gel of nested PCR reaction mixtures that show correct integration at of the 5' and 3' ends of the antibiotic resistance cassette.
Figure 9C:
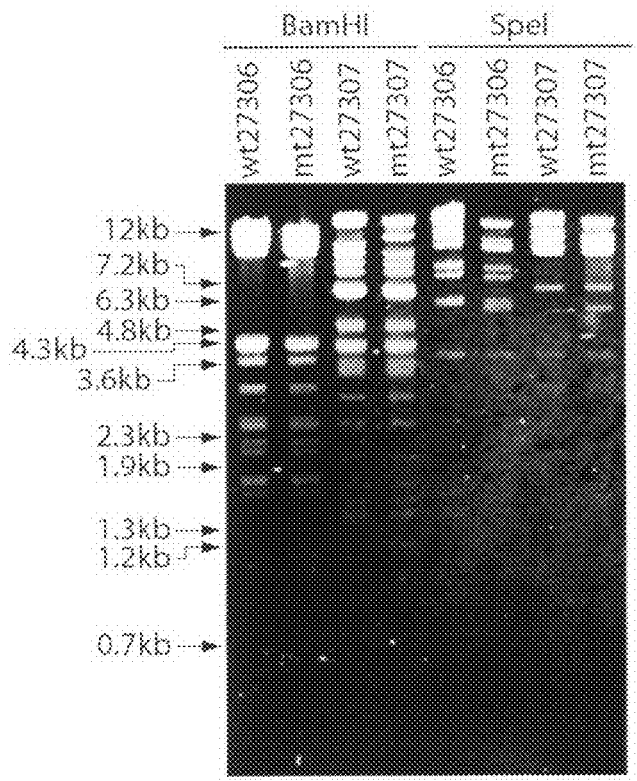
FIG. 9C is a picture of a gel of a restriction digestion of DNA from wild-type (WT) and modified BACs.
Figure 9D:
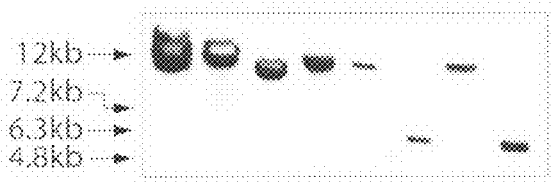
FIG. 9D is a picture of a DNA blot of the gel in FIG. 9C with the probe indicated in FIG. 9A.
Figure 13A:
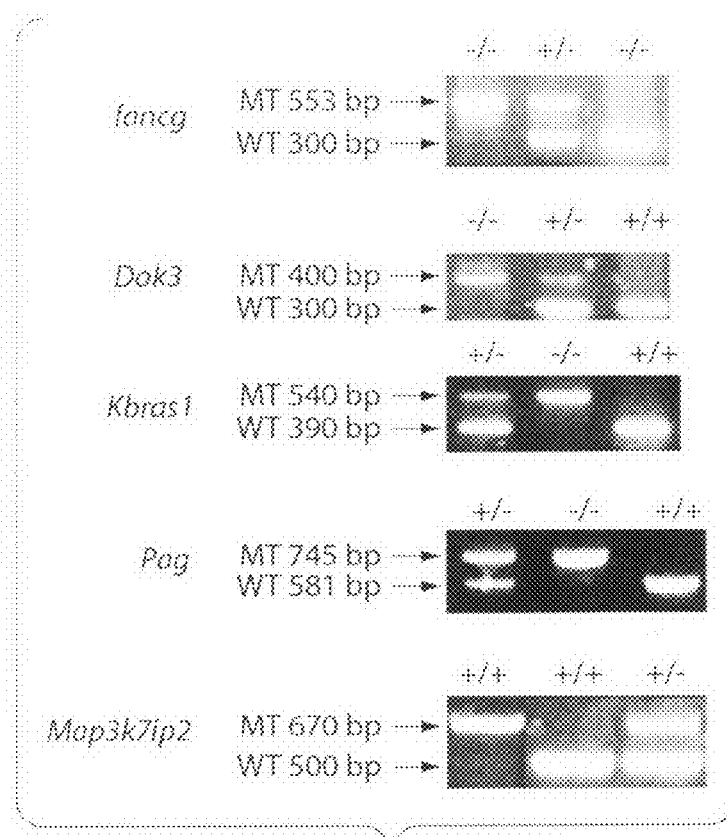
FIGS. 13A-13C illustrate the generation of knockout mice. Genotyping of mouse tail genomic DNA by PCR with primers amplifying the wild type (WT) locus and the mutant (MT) locus is shown in FIG. 13A. RT-PCR analysis of mRNA extracted from mouse spleenocytes with primers amplifying wild type gene transcripts and primers amplifying coding regions of either β2 microbulin (300 bp) or caspase-8 (500 bp) mRNAs as internal controls is shown in FIG. 13B. Analysis of genomic markers within 100 kb of the targeting site is depicted in 13C. Distance of the markers from the targeting site and the sizes of the PCR fragments are indicated. Some markers (M9 for fancg/xrcc9 locus and M3 for iκβras-1 locus) are absent in corresponding BACs, suggesting that these markers are outside of the genomic inserts of the BACs.
Figure 13B:
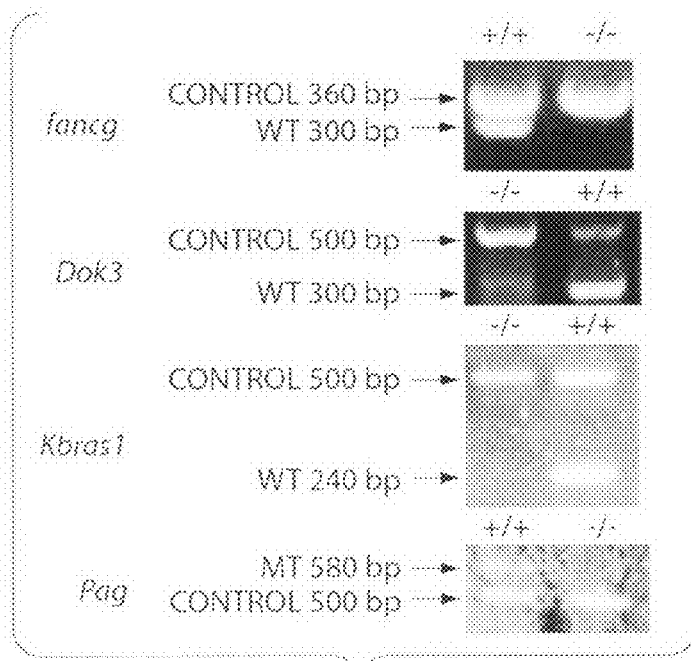
Figure 13C:
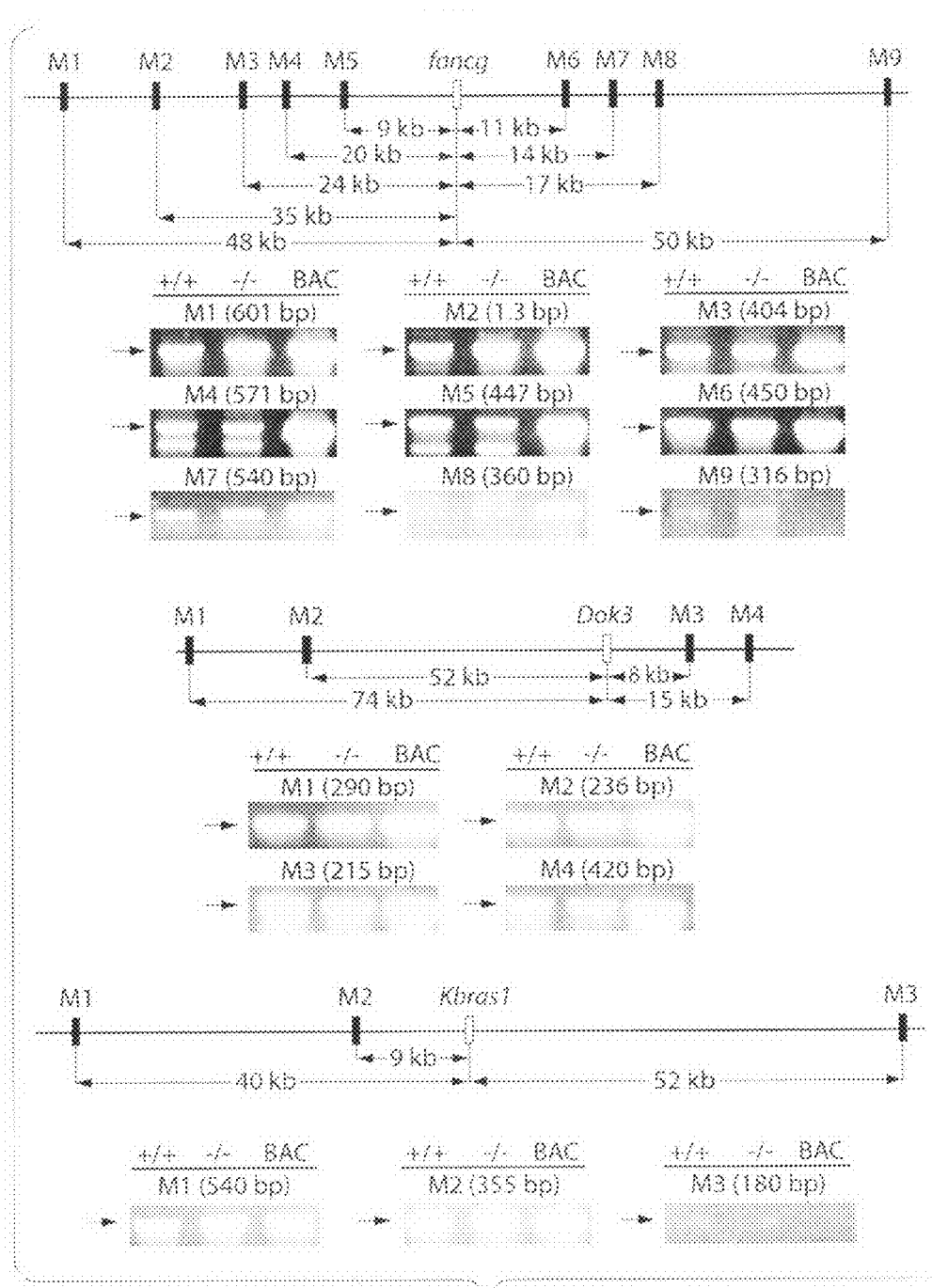

To confirm that the ES clones identified by FISH represented correct targeting events, several ES clones were microinjected into C57BL6 blastocysts, and mice were bred to homozygosity according to standard procedures (DePamphilis, supra). All mice strains were raised and maintained with standard protocols approved by Massachusetts General Hospital. For PCR genotyping, mouse tail genomic DNA was extracted according to standard protocols (DePamphilis, supra), and PCR reactions were performed as described for competitive PCR. We obtained one germline-transmission competent chimera for fancg/xrcc9. The resulting mice had homozygous mutations, as indicated by genomic PCR genotyping (FIGS. 7A and 7B). To evaluate the locus integrity surrounding the targeted site, genomic markers within 100 kb flanking the DNA targeting site were amplified from both wild type and mutant mice. As shown in FIG. 13C, all the markers tested are preserved in the mutant mice, suggesting that an intact BAC can replace the endogenous gene locus by homologous gene recombination without adventitious deletion by undesired recombination between repeated sequence elements in the BAC arms.

Phenotype analysis of fancg/xrcc9 deficient mice is described by Yang et al., (Blood 98:3435-3440, 2001). In contrast, we did not obtain any correctly targeted clones from 192 colonies using conventional procedures to target fancg/xrcc9.

Generation of Additional Knock-out Mice—IκβrasI, dok-3/dok-L, Maguin-1, Cask, CNK, and TIM-3

Figure 6A:
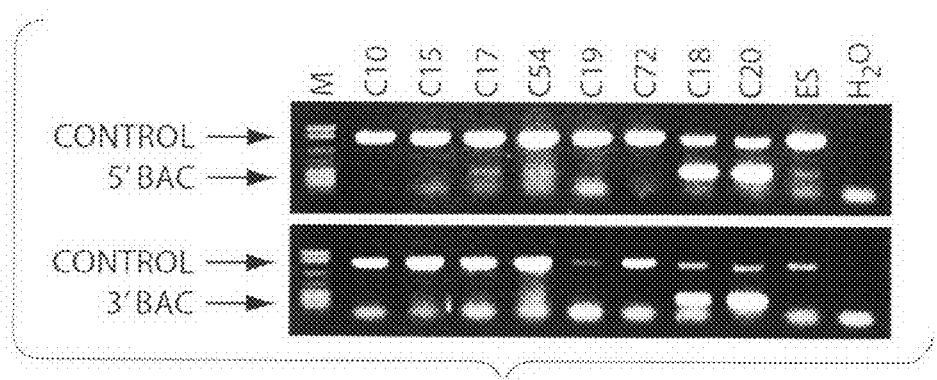
FIGS. 6A and 6B illustrate the identification of dok3/dok-L targeted ES cells.
Figure 6B:
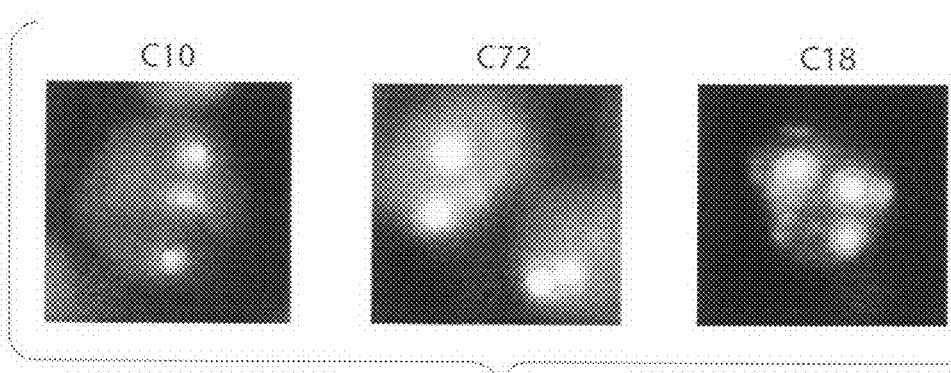

BACs containing mutations in Iκβras1, dok-3/dok-L, pag/cbp, and tab 2 were also used to modify mouse ES cells as described above (FIGS. 5A-8D, 9A-9D, and 13A-13C). We found that the PCR data did not always correlate with the FISH data. For example in targeting the dok-3/dok-L gene, we discovered that clone C10 did not contain BAC vector sequences as judged by PCR (FIG. 6A) but had three signals as observed by FISH (FIG. 6B). These results suggest that FISH can determine true gene replacement events while competitive PCR only serves as a primary screening method to reduce the number of FISH experiments to be conducted.

Several ES clones identified by FISH were injected into mice blastocysts and bred to produce homozygous mice. We have obtained viable mice homozygous for disrupted Iκβras, dok-3/dok-L, and pag/cbp genes (FIGS. 13A and 13B). Breeding of heterozygous TAB2 mutant mice has not resulted in viable homozygous offspring, but homozygous embryos have been detected at Day 9.5 (FIGS. 13A and 13B). To date, all ES clones that have shown germ line transmission have yielded homozygous mice and the frequency of obtaining homozygous mice from ES cells targeted by the approach (BAC-FISHing) is 100%.

We also targeted two X-chromosomal genes, cask and maguin-1. Since there is only one copy of them in ES cells, the wild type locus was disrupted in the mutant clones as judged by genomic PCR (see FIGS. 15 and 16).

Cnk and tim-3 knockouts may also be generated using the same method. In this regard, heterozygous mice from two selected ES clones of each mutant genes may be bred to homozygosity.

The results of several experiments are also summarized in FIG. 14. Approximately, $1-2 \times 10^3$ G418 resistant colonies could generally be obtained from electroporation of $10^7$ cells. For the five genes studied, the average effective targeting efficiency was 15%, and the estimated absolute targeting efficiency was around $10^{-5}$ without selection enrichment. Historical gene targeting efficiencies vary from $10^{-3}$ to undetectable, depending on the locus targeted, vector design, and selection methods (Bollag et al., Annu. Rev. Genet 23:199-225, 1989). Some reports suggest that the average efficiency is closer to $10^{-6}$ to $10^{-7}$, which is the mean targeting efficiency of the well-studied hprt locus (Capecchi et al., Science 244:1288-1292, 1989). Our mean ratio of homologous to nonhomologous recombination events is $1.5 \times 10^{-1}$, while the corresponding ratio for traditional methods is between $10^{-2}$ and $10^{-5}$ (Reid et al., Mol. Cell Biol. 11:2769-2777, 1991). The efficiency achieved using the methods of the present invention is close to the homologous recombination rate found in nuclear extracts from murine embryonic fibroblast cells (Thyagarajan et al., Nucleic Acids Res. 24:4084-4091, 1996).

Generation of Conditional Knockouts, Knock-ins, and Chromosomal Alterations

If desired, a cell can be genetically modified such that a deletion mutation only occurs in certain cells of a mammal generated using the genetically modified donor cell. In particular, the donor cell has two recombinase signal sequences (e.g., recombinase signal sequences within introns that flank one or more exons to be deleted) and recombination occurs between the recombinase signal sequences in cells of a predetermined cell type of the resulting mammal. For example, the donor cell may be genetically modified to encode a recombinase under the control of a promoter specific for the predetermined cell type such that the recombinase is only expressed and recombination only occurs in that cell type of mammal. Alternatively, a mammal modified to contain the recombinase signal sequences can be mated with a mammal modified to express the recombinase under the control of a promoter specific for the predetermined cell type.

Figure 17A:
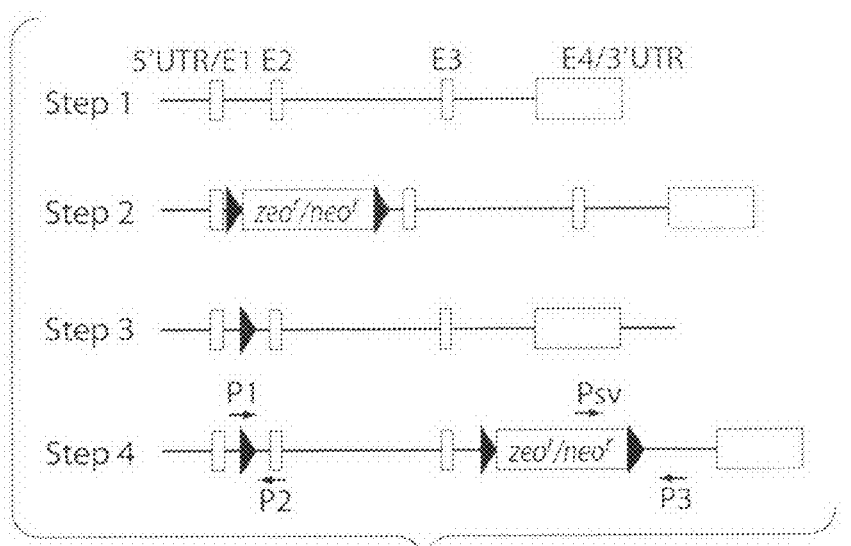
FIGS. 17A-17C illustrate the generation of conditional tiap knockout nice.
Figure 17B:
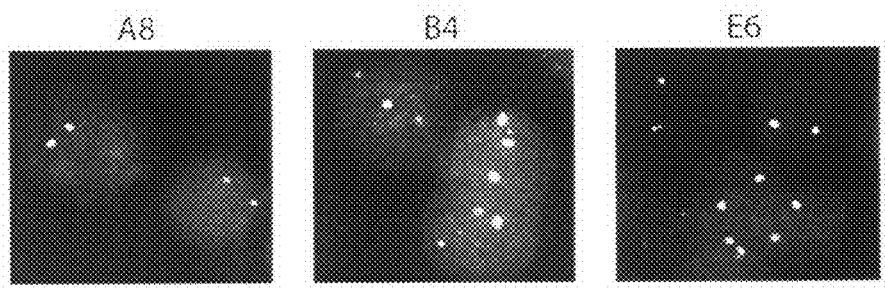
Figure 17C:
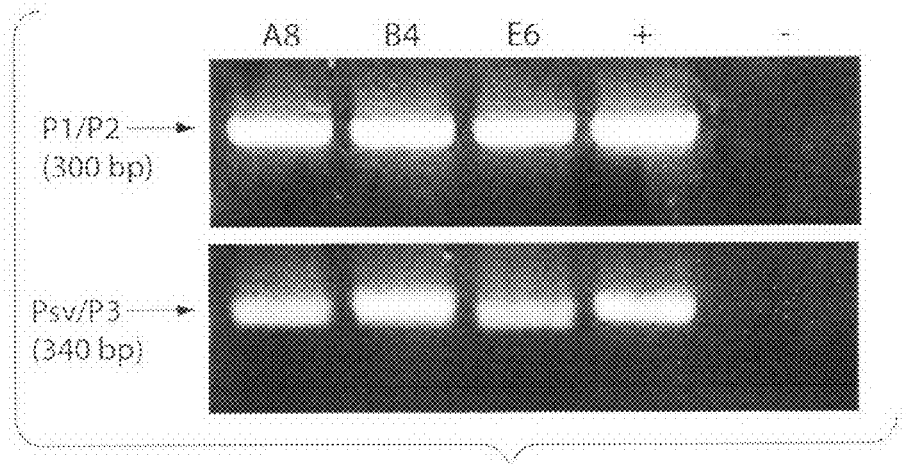

We have created a tiap conditional knockout construct using the approach described above. First, the FRT flanked zeo/neo marker was inserted into intron 1 (FIG. 17A, step 2) and correctly modified P1 s were transduced into a bacteria host expressing the yeast site-specific recombinase flp to remove the zeo/neo marker (FIG. 17A, step 3). The FRT flanked zeo/neo marker was next inserted into intron 3 (FIG. 17A, step 4). The FRT sites were therefore positioned into designated introns by sequential P1 modification. The modified P1 was next used to target ES cells and correctly targeted ES cells were selected by BAC-FISHing (FIG. 17B). All the FRT sites had been faithfully integrated into the ES genome (FIG. 17C). Clones A8 and B6 can be injected into blastocyst as described above. Following the generation of homozygous mice, mice may be bred into a mouse strain with a lck-flp transgene to express flp.

Knock-in mutations can be generated by including a nucleic acid such as a reporter gene or nucleic acid encoding a detectable protein between the regions of homology in the linear DNA fragment used to generate the modified BAC. Desirably, the reporter gene is integrated under the control of an endogenous promoter of interest. The nucleic acid encoding a detectable protein is desirably integrated in-frame with an endogenous nucleic acid encoding a protein of interest for the generation of a fusion nucleic acid the encodes a fusion protein with the detectable protein and the protein of interest.

For the generation of chromosomal alterations, a genetically modified cell is generated with two recombinase signal sequences. If the recombinase signal sequences are in the same endogenous chromosome of the cell, recombination eliminates the DNA between the recombinase signal sequences. If the recombinase signal sequences are in different endogenous chromosome of the cell, recombination results in chromosomal translocation between the recombinase signal sequences. Chromosome deletions can also be generated by using a linear DNA molecule that has two regions of homology that correspond to regions of the endogenous chromosome that flank the DNA to be deleted (e.g., a single gene or a cluster of genes to be deleted). The cells and mammals generated using this linear DNA molecule have the desired deletion mutation. If desired, this method can be repeated to delete an additional region beside the first deletion site.

Optional Modifications to Further Increase the Efficiency of the Present Methods To reduce the time required to generate bacteria containing both a BAC and the pBADλredαβ plasmid, the pBADλredαβ plasmid can be transferred to bacteria containing the BAC by conjugation. In particular, we have discovered that plasmids containing either the OriT region from F' or the bom-mob complex from the ColE1 plasmid can by mobilized by a male E. coli strain (e.g., XL-1Blue, an F'-bearing strain) to the BAC host strain DH10B through conjugation. In both cases, the small plasmid is preferentially transferred relative to the mobilizing F'. To further reduce the contribution of episomal elements, the small plasmids can be introduced into an Hfr strain of E. coli. We have generated plasmids that contain oriT in the pBADλredαβ plasmid or that contain bom-mob of ColE1, the p15A replicon from plasmid pACYC184, and λred αβ or λred αβ plus PI-SceI under the control of either the Ara BAD promoter or the lac uv5 promoter. These plasmids can be introduced into the BAC host by growing the two strains together for one hour and selecting for ampicillin and chloramphenicol double resistant colonies, or kanamycin and chloramphenicol resistant colonies, depending on the resistance of the BAC plasmid.

If desired, a temperature sensitive replicon can be used so that cells containing only the modified BAC can be isolated by killing cells containing the pBADλredαβ plasmid by shifting the cultures to a higher temperature. In particular, the ColE1 replicon on the pBADλredαβ plasmid can be replaced with the temperature sensitive (ts) replicon from pSC101. Cells with this pBADλredαβ plasmid are unable to grow at 42° C., so elevated temperatures can be used to separate this plasmid from the modified BAC.

If desired, the linear DNA molecule used for generation of the modified BAC can be generated in vivo by cleavage of a circular fragment containing the sequence of the linear DNA fragment flanked by SceI sites. The VDE/PI-SceI system can be used according to the manufacturer's instructions for this procedure. Thus, a bacterial strain containing a BAC, a bacterial strain containing the pBADλredαβ plasmid, and a bacterial plasmid with the sequence of the linear DNA fragment flanked by SceI sites can be grown together, and the BAC and the two plasmids can be transferred into the same bacteria by conjugation antibiotic selection. This method may eliminate the need for electroporation of competent cells and allow library screening and BAC modification to be performed in a single step.

Generation of Other Genetically Modified Mammals

The methods described above for the genetic modification of mice can generally be applied to the genetic modification of any non-human mammal. In particular, an artificial chromosome (e.g., a BAC) containing a genomic insert from another mammal can be purchased or constructed using standard methods (Ausubel et al., supra). The BAC can be homologously recombined with a linear DNA molecule containing a positive selection marker flanked by two regions with homology to a nucleic acid in the BAC as described above. The resulting modified BAC can be used to alter the genome of cells from the same genus or species as the source of the genomic insert in the BAC. A variety of cells can be modified including embryonic, fetal, and adult differentiated or undifferentiated cells. The resulting modified cells can be used in any standard method for the generation of a cloned or chimeric mammal. For example, genetically modified ES cells can be injected into an embryo for the generation of chimeric mammals as described above. Alternatively, an embryonic or somatic cell or a nucleus from the cell (e.g., an ungulate cell) can be inserted into an oocyte (e.g., an enucleated oocyte). After activation of the oocyte, the oocyte is placed in culture medium for an appropriate amount of time to allow development of the resulting embryo. At the two cell stage or a later stage, the embryo is transferred into a foster recipient female for development to term (see, for example, U.S. Pat. Nos. 4,994,384; 6,077,710; 5,453,366; 5,945,577; 6,258,998; and 5,057,420; Wakayama et al., PNAS 96:14984-14989, 1999; Wakayama et al., Nature Genetics 24:108-109, 2000; and Stice and Keefer, Biology of Reproduction 48: 715-719, 1993).

Exemplary Applications of the Present Methods

The mammals produced by any of the methods of the present invention can be used as animal models to identify candidate compounds that modulate the expression of a nucleic acid or protein of interest or that are useful for the treatment or prevention of a disease. For example, a mammal can be genetically modified to express a reporter gene under the control of a promoter of interest by the integration of a knock-in cassette containing a reporter gene that is flanked by a region homologous to the promoter of interest and another region of homology. Candidate compounds are administered to this mammal to determine whether they modulate the activity of the promoter of interest and thus are useful for the treatment of a disease associated with a nucleic acid operably linked to the promoter of interest. Alternatively, a mammal can be genetically modified to express a fusion protein that includes a detectable protein and a protein of interest. This mammal is generated, e.g., by the integration of a knock-in cassette containing two regions homologous to a nucleic acid of interest (i.e., the nucleic acid encoding the protein of interest) flanking a nucleic acid encoding the detectable protein. Candidate compounds are administered to this mammal to determine if they modulate the expression of this fusion protein in vivo. Such compounds may be useful for the treatment of a disease associated with the protein of interest.

The present methods can also be used to generate animal models of various diseases. In particular, one or more mutations associated with a disease can be introduced into a mammal (e.g., a mouse, ungulate, or primate) as described herein. Candidate compounds can be administered to these mammals to determine whether the compounds ameliorate or prevent a symptom or other physiological effect associated with the disease. Exemplary mutations associated with cancer or diabetes are described by Ruediger et al. (Oncogene 20:10-15, 2001) and Yokoi et al. (Nature Genetics 31:391-394, 2002), respectively. Chromosomal translocations associated with cancer (e.g., acute myelogenous leukemia) are also described by the following references: Kuehl et al., Nature Reviews Cancer 2(3):175-87, 2002; Dyer et al., Leukemia 16(6):973-84, 2002; Gojo et al., Cancer Treatment & Research 108:231-55, 2001; Padua et al., Cancer Treatment & Research 108: 111-57, 2001; Falini et al., Blood 99(2):409-26, 2002; Stevenson et al., Advances in Cancer Research 83:81-116, 2001; Swerdlow et al., Human Pathology 33(1):7-20, 2002; Chakraborty et al., Journal of Cellular Biochemistry 82(2): 310-25, 2001; Kelly et al., Current Opinion in Oncology 14(1):10-8, 2002; Falini et at, British Journal of Haematology 114(4):741-60, 2001; Davila et al., Advances in Cancer Research 81:61-92, 2001; Sturzl et al., Advances in Cancer Research 81:125-59, 2001; Arvand et al., Oncogene 20(40): 5747-54, 2001; Barr et al., Oncogene 20(40):5736-46, 2001; Seidel et al., Oncogene 20(40):5718-25, 2001; Aspland et al., Oncogene 20(40):5708-17, 2001; Alcalay et al., Oncogene 20(40):5680-94, 2001; Licht et al., Oncogene 20(40):5660-79, 2001; Duyster et al., Oncogene 20(40):5623-37, 2001; Bergsagel et al., Oncogene 20(40):5611-22, 2001; Boxer et al., Oncogene 20(40):5595-610, 2001; Kuppers et al., Oncogene 20(40):5580-94, 2001; Mullauer et al., Mutation Research 488(3):211-31, 2001; Morris et al., British Journal of Haematology 113(2):275-95, 2001; Lamorte et al., Surgical Oncology Clinics of North America 10(2):271-88, viii, 2001; Maru, International Journal of Hematology 73(3):308-22, 2001; Sattler et al, International Journal of Hematology 73(3):278-91, 2001; Holyoake, British Journal of Haematology 113(1):11-23, 2001; Bower, British Journal of Haematology 112(4):863-73, 2001; Crans et al., Leukemia 15(3): 313-31, 2001; Lee, British Journal of Haematology 111(4): 993-1009, 2000; Mavrothalassitis et al., Oncogene 19(55): 6524-32, 2000; Garcia-Manero et al., Hematology—Oncology Clinics of North America 14(6):1381-96, x-xi, 2000; Larson, Hematology—Oncology Clinics of North America 14(6):1367-79, x, 2000; Thiebaut et al., Hematology—Oncology Clinics of North America 14(6): 1353-66, x, 2000; Durrant et al., Hematology Oncology Clinics of North America 14(6):1327-52, 2000; Faderl et al., Hematology Oncology Clinics of North America 14(6):1267-88, 2000; Drexler et al, Leukemia 14(9):1533-59, 2000; Pui et al., British Journal of Haematology 109(1):13-23, 2000; and Dierlamm et al., Hematological Oncology 18(1):1-13, 2000.

The genetically modified mammals of the invention are also useful for target validation to confirm that a nucleic acid of interest is associated with a disease, disorder, or condition. For example, one or more symptoms associated with the disease, disorder, or condition can be compared between a mammal having a mutation in the nucleic acid of interest or having a mutation that alters the expression of a nucleic acid of interest (e.g., a mutation in a promoter or the insertion of a exogenous promoter) and a control mammal without the mutation. Exemplary nucleic acids include nucleic acids that are thought to promote cancer such as possible oncogenes; genes that enhance cell proliferation, invasion, or metastasis; genes that inhibit apoptosis; and pro-angiogenesis genes.

Moreover, the present methods can be used as an alternative to conventional gene therapy methods to correct a mutation associated with a disease in cells from a patient (e.g., a human) that are subsequently readministered to the patient or administered to another patient (Kyba et al., Cell. 109(1):29-37 2002; Rideout et al., Cell. 109(1):17-27, 2002). In these applications, cells (e.g., cells from a human patient such as primary cells, bone marrow cells, or blood cells) are genetically modified to replace a region of nucleic acid that has one or more mutations associated with a disease with a nucleic acid segment without the mutation(s). The genetic modification procedure can be repeated, if desired, to correct both alleles of the nucleic acid. Then, standard methods can be used to administer the modified cells into the appropriate area of the patient.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

What is claimed is:

1. A method of producing a genetically modified mammalian cell, said method comprising the steps of:
   (a) inserting into one or more mammalian cells an artificial chromosome comprising a cassette which includes a first region of homology having at least 90% sequence identity to a first region of an endogenous chromosome of said one or more mammalian cells, a selectable marker, and a second region of homology having at least 90% sequence identity to a second region of said endogenous chromosome under conditions that result in homologous recombination between said artificial chromosome and said endogenous chromosome and integration of said cassette into said endogenous chromosome of one or more mammalian cells; and
   (b) selecting a mammalian cell in which said homologous recombination occurs, thereby selecting a genetically modified mammalian cell.

2. A method of producing a genetically modified mammalian cell, said method comprising the steps of:
   (a) culturing a host cell that has (i) a linear DNA molecule comprising a cassette which includes a first region of homology having at least 90% sequence identity to a first region of an endogenous chromosome of said mammalian cell, a selectable marker, and a second region of homology having at least 90% sequence identity to a second region of said endogenous chromosome and (ii) an artificial chromosome comprising a first nucleic acid sequence that has at least 90% sequence identity to said first region of homology and a second nucleic acid sequence that has at least 90% sequence identity to said second region of homology under conditions that result in homologous recombination between said linear DNA molecule and said artificial chromosome, thereby generating an artificial chromosome comprising said cassette;
   (b) inserting into one or more mammalian cells said artificial chromosome comprising said cassette under conditions that result in homologous recombination between said artificial chromosome and said endogenous chromosome and integration of said cassette into said endogenous chromosome of said one or more mammalian cells; and
   (c) selecting a mammalian cell in which said homologous recombination occurs, thereby selecting a genetically modified mammalian cell.

3. The method of claim 2, wherein said linear DNA molecule is introduced into said host cell by transformation.

4. The method of claim 2, wherein, prior to step (a) a circular vector comprising the sequence of said linear DNA molecule is inserted into said host cell and said vector is cleaved to generate said linear DNA molecule inside said host cell.

5. The method of claim 1, wherein said first and second regions of said endogenous chromosome are contiguous.

6. The method of claim 5, wherein said first and second regions of said endogenous chromosome are part of the same exon or the same promoter.

7. The method of claim 1, wherein said first and second regions of said endogenous chromosome are not contiguous.

8. The method of claim 7, wherein said first and second regions of said endogenous chromosome are part of different exons.

9. The method of claim 1, wherein the integration of said cassette into said endogenous chromosome of said one or more mammalian cells reduces the activity of a protein encoded by a nucleic acid of interest that includes said first or said second region of said endogenous chromosome.

10. The method of claim 9, wherein said activity of said protein encoded by said nucleic acid of interest decreases by at least 25%.

11. The method of claim 1, wherein said selectable marker is a reporter gene, and wherein said cassette is integrated into said endogenous chromosome of said one or more mammalian cells such that said reporter gene after integration is operably linked to an endogenous promoter of interest of said one or more mammalian cells, thereby generating a genetically modified mammalian cell that expresses said reporter gene under the control of said promoter.

12. The method of claim 1, wherein said selectable marker is a nucleic acid encoding a detectable protein, and wherein said cassette is integrated into said endogenous chromosome of said one or more mammalian cells such that said nucleic acid after integration is operably linked to an endogenous nucleic acid of said one or more mammalian cells encoding a protein of interest, thereby generating a genetically modified mammalian cell that expresses a fusion protein comprising said detectable protein and protein of interest or fragment thereof.

13. The method of claim 1, wherein said mammalian cell is an embryonic stem cell.

14. The method of claim 1, wherein said mammalian cell is a somatic cell.

* * * * *

UNITED STATES PATENT AND TRADEMARK OFFICE
CERTIFICATE OF CORRECTION

PATENT NO. : 7,518,033 B2
APPLICATION NO. : 10/521634
DATED : April 14, 2009
INVENTOR(S) : Seed et al.

It is certified that error appears in the above-identified patent and that said Letters Patent is hereby corrected as shown below:

IN THE DRAWINGS:
Sheet 13, Fig. 5B, above the bottom left image, add --C68-- and
above the bottom right image, add --ES--;

IN THE SPECIFICATION:
Column 8, Line 60, replace "cartificaial" with --artificial--;

Column 11, Line 29, replace "die" with --the--;

Column 14, Line 36, replace "nice" with --mice--;

Column 17, Line 50, replace "replace" with --replaced--
Line 64, delete the first instance of "through";

Column 19, line 5, replace "chloramphenical" with --chloramphenicol--
Line 35, replace "endonuleases" with --endonucleases--;

Column 20, Line 27, replace "gtctttgaacftatcaatctc" with --gtctttgaacttatcaatctc--;

Column 25, Line 62, replace "chloramiphicol" with --chloramphenicol--.

Signed and Sealed this

Thirty-first Day of August, 2010

David J. Kappos
*Director of the United States Patent and Trademark Office*

SEQUENCE LISTING

<160> NUMBER OF SEQ ID NOS: 47

<210> SEQ ID NO 1
<211> LENGTH: 22
<212> TYPE: DNA
<213> ORGANISM: Artificial Sequence
<220> FEATURE:
<223> OTHER INFORMATION: Primers

<400> SEQUENCE: 1

```
ggccagggtg ttgtccggca cc                                              22
```

<210> SEQ ID NO 2
<211> LENGTH: 20
<212> TYPE: DNA
<213> ORGANISM: Artificial Sequence
<220> FEATURE:
<223> OTHER INFORMATION: Primers

<400> SEQUENCE: 2

```
aaggttgggc ttcggaatcg                                                 20
```

<210> SEQ ID NO 3
<211> LENGTH: 23
<212> TYPE: DNA
<213> ORGANISM: Artificial Sequence
<220> FEATURE:
<223> OTHER INFORMATION: Primers

<400> SEQUENCE: 3

```
acagatgcgt aaggagaaaa tac                                             23
```

<210> SEQ ID NO 4
<211> LENGTH: 23
<212> TYPE: DNA
<213> ORGANISM: Artificial Sequence
<220> FEATURE:
<223> OTHER INFORMATION: Primers

<400> SEQUENCE: 4

```
cgccctatag tgagtcgtat tac                                             23
```

<210> SEQ ID NO 5
<211> LENGTH: 23
<212> TYPE: DNA
<213> ORGANISM: Artificial Sequence
<220> FEATURE:
<223> OTHER INFORMATION: Primers

<400> SEQUENCE: 5

```
atagtgtcac ctaaatagct tgg                                             23
```

<210> SEQ ID NO 6
<211> LENGTH: 23
<212> TYPE: DNA
<213> ORGANISM: Artificial Sequence
<220> FEATURE:
<223> OTHER INFORMATION: Primers

<400> SEQUENCE: 6

```
ggcacgacag gtttcccgac tgg                                             23
```

<210> SEQ ID NO 7
<211> LENGTH: 21
<212> TYPE: DNA
<213> ORGANISM: Artificial Sequence
<220> FEATURE:
<223> OTHER INFORMATION: Primers

<400> SEQUENCE: 7

```
gaggacatct ttccctcagg c                                               21
```

<210> SEQ ID NO 8
<211> LENGTH: 20
<212> TYPE: DNA
<213> ORGANISM: Artificial Sequence

```
<220> FEATURE:
<223> OTHER INFORMATION: Primers

<400> SEQUENCE: 8
cagaggctct gagtaagacc                                               20

<210> SEQ ID NO 9
<211> LENGTH: 23
<212> TYPE: DNA
<213> ORGANISM: Artificial Sequence
<220> FEATURE:
<223> OTHER INFORMATION: Primers

<400> SEQUENCE: 9
ccgtcttcca gccacggagc ggg                                           23

<210> SEQ ID NO 10
<211> LENGTH: 24
<212> TYPE: DNA
<213> ORGANISM: Artificial Sequence
<220> FEATURE:
<223> OTHER INFORMATION: Primers

<400> SEQUENCE: 10
ggcgatatct gccgttggtt ctaa                                          24

<210> SEQ ID NO 11
<211> LENGTH: 22
<212> TYPE: DNA
<213> ORGANISM: Artificial Sequence
<220> FEATURE:
<223> OTHER INFORMATION: Primers

<400> SEQUENCE: 11
ccgaattcca ggctactgga aa                                            22

<210> SEQ ID NO 12
<211> LENGTH: 24
<212> TYPE: DNA
<213> ORGANISM: Artificial Sequence
<220> FEATURE:
<223> OTHER INFORMATION: Primers

<400> SEQUENCE: 12
cccggatccc acctcctctc tagg                                          24

<210> SEQ ID NO 13
<211> LENGTH: 24
<212> TYPE: DNA
<213> ORGANISM: Artificial Sequence
<220> FEATURE:
<223> OTHER INFORMATION: Primers

<400> SEQUENCE: 13
ggcgaagctt tctgagcctt tagt                                          24

<210> SEQ ID NO 14
<211> LENGTH: 19
<212> TYPE: DNA
<213> ORGANISM: Artificial Sequence
<220> FEATURE:
<223> OTHER INFORMATION: Primers

<400> SEQUENCE: 14
tggctaaatt cactaagtg                                                19
```

<210> SEQ ID NO 15
<211> LENGTH: 24
<212> TYPE: DNA
<213> ORGANISM: Artificial Sequence
<220> FEATURE:
<223> OTHER INFORMATION: Primers

<400> SEQUENCE: 15
cctctgagga tctgctacta ctgc                                          24

<210> SEQ ID NO 16
<211> LENGTH: 24
<212> TYPE: DNA
<213> ORGANISM: Artificial Sequence
<220> FEATURE:
<223> OTHER INFORMATION: Primers

<400> SEQUENCE: 16
gtgtacacct ggactaacac ggac                                          24

<210> SEQ ID NO 17
<211> LENGTH: 22
<212> TYPE: DNA
<213> ORGANISM: Artificial Sequence
<220> FEATURE:
<223> OTHER INFORMATION: Primers

<400> SEQUENCE: 17
gggatggaag actgtgaaac gc                                            22

<210> SEQ ID NO 18
<211> LENGTH: 21
<212> TYPE: DNA
<213> ORGANISM: Artificial Sequence
<220> FEATURE:
<223> OTHER INFORMATION: Primers

<400> SEQUENCE: 18
gtctttgaac ttatcaatct c                                             21

<210> SEQ ID NO 19
<211> LENGTH: 22
<212> TYPE: DNA
<213> ORGANISM: Artificial Sequence
<220> FEATURE:
<223> OTHER INFORMATION: Primers

<400> SEQUENCE: 19
aggtggcaat cgttgtgtta gg                                            22

<210> SEQ ID NO 20
<211> LENGTH: 21
<212> TYPE: DNA
<213> ORGANISM: Artificial Sequence
<220> FEATURE:
<223> OTHER INFORMATION: Primers

<400> SEQUENCE: 20
ctggatttgc tctgggctga g                                             21

<210> SEQ ID NO 21
<211> LENGTH: 21
<212> TYPE: DNA
<213> ORGANISM: Artificial Sequence
<220> FEATURE:
<223> OTHER INFORMATION: Primers

<400> SEQUENCE: 21
gctggcgcaa agtgggtctc g                                            21

<210> SEQ ID NO 22
<211> LENGTH: 23
<212> TYPE: DNA
<213> ORGANISM: Artificial Sequence
<220> FEATURE:
<223> OTHER INFORMATION: Primers

<400> SEQUENCE: 22
ccgggaaggc cagctgacag atg                                          23

<210> SEQ ID NO 23
<211> LENGTH: 21
<212> TYPE: DNA
<213> ORGANISM: Artificial Sequence
<220> FEATURE:
<223> OTHER INFORMATION: Primers

<400> SEQUENCE: 23
gaggacatct ttccctcagg c                                            21

<210> SEQ ID NO 24
<211> LENGTH: 20
<212> TYPE: DNA
<213> ORGANISM: Artificial Sequence
<220> FEATURE:
<223> OTHER INFORMATION: Primers

<400> SEQUENCE: 24
cagaggctct gagtaagacc                                              20

<210> SEQ ID NO 25
<211> LENGTH: 22
<212> TYPE: DNA
<213> ORGANISM: Artificial Sequence
<220> FEATURE:
<223> OTHER INFORMATION: Primers

<400> SEQUENCE: 25
aataacctgg atgcctgctg cg                                           22

<210> SEQ ID NO 26
<211> LENGTH: 22
<212> TYPE: DNA
<213> ORGANISM: Artificial Sequence
<220> FEATURE:
<223> OTHER INFORMATION: Primers

<400> SEQUENCE: 26
gaaggttgat aggcttgctg ag                                           22

<210> SEQ ID NO 27
<211> LENGTH: 23
<212> TYPE: DNA
<213> ORGANISM: Artificial Sequence
<220> FEATURE:
<223> OTHER INFORMATION: Primers

<400> SEQUENCE: 27
taatcccatg aaccctcagc aag                                          23

<210> SEQ ID NO 28

<211> LENGTH: 23
<212> TYPE: DNA
<213> ORGANISM: Artificial Sequence
<220> FEATURE:
<223> OTHER INFORMATION: Primers

<400> SEQUENCE: 28
gcatcatcag atcccatact cag                                              23

<210> SEQ ID NO 29
<211> LENGTH: 24
<212> TYPE: DNA
<213> ORGANISM: Artificial Sequence
<220> FEATURE:
<223> OTHER INFORMATION: Primers

<400> SEQUENCE: 29
attctttcag aagacagcac gctg                                             24

<210> SEQ ID NO 30
<211> LENGTH: 23
<212> TYPE: DNA
<213> ORGANISM: Artificial Sequence
<220> FEATURE:
<223> OTHER INFORMATION: Primers

<400> SEQUENCE: 30
gcgtccaccg gtcccttctg cag                                              23

<210> SEQ ID NO 31
<211> LENGTH: 26
<212> TYPE: DNA
<213> ORGANISM: Artificial Sequence
<220> FEATURE:
<223> OTHER INFORMATION: Primers

<400> SEQUENCE: 31
cgggtcttct tcccgagact tgtatg                                           26

<210> SEQ ID NO 32
<211> LENGTH: 19
<212> TYPE: DNA
<213> ORGANISM: Artificial Sequence
<220> FEATURE:
<223> OTHER INFORMATION: Primers

<400> SEQUENCE: 32
aggtattgga agaaatttc                                                   19

<210> SEQ ID NO 33
<211> LENGTH: 20
<212> TYPE: DNA
<213> ORGANISM: Artificial Sequence
<220> FEATURE:
<223> OTHER INFORMATION: Primers

<400> SEQUENCE: 33
ggccttactt cagactcatg                                                  20

<210> SEQ ID NO 34
<211> LENGTH: 22
<212> TYPE: DNA
<213> ORGANISM: Artificial Sequence
<220> FEATURE:
<223> OTHER INFORMATION: Primers

<400> SEQUENCE: 34

-continued ttggctcatc cgtgttcttt tg                                        22

<210> SEQ ID NO 35
<211> LENGTH: 22
<212> TYPE: DNA
<213> ORGANISM: Artificial Sequence
<220> FEATURE:
<223> OTHER INFORMATION: Primers

<400> SEQUENCE: 35
aggtcttgat gactgtttgc ag                                        22

<210> SEQ ID NO 36
<211> LENGTH: 23
<212> TYPE: DNA
<213> ORGANISM: Artificial Sequence
<220> FEATURE:
<223> OTHER INFORMATION: Primers

<400> SEQUENCE: 36
cagtgcacac aaaaggtcaa ctg                                       23

<210> SEQ ID NO 37
<211> LENGTH: 22
<212> TYPE: DNA
<213> ORGANISM: Artificial Sequence
<220> FEATURE:
<223> OTHER INFORMATION: Primers

<400> SEQUENCE: 37
ttatggctta gaaacagaaa tc                                        22

<210> SEQ ID NO 38
<211> LENGTH: 25
<212> TYPE: DNA
<213> ORGANISM: Artificial Sequence
<220> FEATURE:
<223> OTHER INFORMATION: Primers

<400> SEQUENCE: 38
cctgtccaac caagcaagaa gactc                                     25

<210> SEQ ID NO 39
<211> LENGTH: 21
<212> TYPE: DNA
<213> ORGANISM: Artificial Sequence
<220> FEATURE:
<223> OTHER INFORMATION: Primers

<400> SEQUENCE: 39
atgatgccct acaggactat c                                         21

<210> SEQ ID NO 40
<211> LENGTH: 20
<212> TYPE: DNA
<213> ORGANISM: Artificial Sequence
<220> FEATURE:
<223> OTHER INFORMATION: Primers

<400> SEQUENCE: 40
aggcaaagct gcaggaactg                                           20

<210> SEQ ID NO 41
<211> LENGTH: 20
<212> TYPE: DNA

```
<213> ORGANISM: Artificial Sequence
<220> FEATURE:
<223> OTHER INFORMATION: Primers

<400> SEQUENCE: 41
agggacatcc cagatctgag                                              20

<210> SEQ ID NO 42
<211> LENGTH: 22
<212> TYPE: DNA
<213> ORGANISM: Artificial Sequence
<220> FEATURE:
<223> OTHER INFORMATION: Primers

<400> SEQUENCE: 42
ctctggactg ccacttttaa ag                                           22

<210> SEQ ID NO 43
<211> LENGTH: 23
<212> TYPE: DNA
<213> ORGANISM: Artificial Sequence
<220> FEATURE:
<223> OTHER INFORMATION: Primers

<400> SEQUENCE: 43
ccacaaacct ctatgtctca aag                                          23

<210> SEQ ID NO 44
<211> LENGTH: 24
<212> TYPE: DNA
<213> ORGANISM: Artificial Sequence
<220> FEATURE:
<223> OTHER INFORMATION: Primers

<400> SEQUENCE: 44
agccttatta cactggccaa cttg                                         24

<210> SEQ ID NO 45
<211> LENGTH: 26
<212> TYPE: DNA
<213> ORGANISM: Artificial Sequence
<220> FEATURE:
<223> OTHER INFORMATION: Primers

<400> SEQUENCE: 45
gtggtgacgc catcatggga gctccg                                       26

<210> SEQ ID NO 46
<211> LENGTH: 17
<212> TYPE: DNA
<213> ORGANISM: Artificial Sequence
<220> FEATURE:
<223> OTHER INFORMATION: Primers

<400> SEQUENCE: 46
ctcagctaat tatcgag                                                 17

<210> SEQ ID NO 47
<211> LENGTH: 22
<212> TYPE: DNA
<213> ORGANISM: Artificial Sequence
```

```
<220> FEATURE:
<223> OTHER INFORMATION: Primers

<400> SEQUENCE: 47
cgggttgtca tcgggttccc ag                                                   22
```